US011559553B2

(12) United States Patent
Daniel et al.

(10) Patent No.: US 11,559,553 B2
(45) Date of Patent: Jan. 24, 2023

(54) PRODUCTS DERIVED FROM AMNIOTIC FLUID AND METHODS OF USE

(71) Applicant: StimLabs LLC, Roswell, GA (US)

(72) Inventors: John Daniel, Milton, GA (US); Richard A. Berg, Arroyo Grande, CA (US); Sarah Griffiths, Atlanta, GA (US)

(73) Assignee: StimLabs LLC, Roswell, GA (US)

( * ) Notice: Subject to any disclaimer, the term of this patent is extended or adjusted under 35 U.S.C. 154(b) by 47 days.

(21) Appl. No.: 15/739,567

(22) PCT Filed: Jun. 27, 2016

(86) PCT No.: PCT/US2016/039668
§ 371 (c)(1),
(2) Date: Dec. 22, 2017

(87) PCT Pub. No.: WO2017/003954
PCT Pub. Date: Jan. 5, 2017

(65) Prior Publication Data
US 2018/0311283 A1    Nov. 1, 2018

Related U.S. Application Data

(60) Provisional application No. 62/185,605, filed on Jun. 27, 2015.

(51) Int. Cl.
A61K 35/50     (2015.01)
A61K 8/98      (2006.01)
(Continued)

(52) U.S. Cl.
CPC .............. A61K 35/50 (2013.01); A61K 8/982 (2013.01); A61K 9/0014 (2013.01);
(Continued)

(58) Field of Classification Search
CPC ...... A61K 35/50; A61K 31/728; A61K 8/982; A61K 9/0021; A61K 9/0048; A61K 2800/91; C07K 14/435
See application file for complete search history.

(56) References Cited

U.S. PATENT DOCUMENTS 7,871,646 B2    1/2011   Ghinelli
7,968,336 B2    6/2011   Atala et al.
(Continued)

FOREIGN PATENT DOCUMENTS

WO    2017003954 A1    1/2017

OTHER PUBLICATIONS

Erickson et al. "Size and Shape of Protein Molecules at the Nanometer Level Determined by Sedimentation, Gel Filtration, and Electron Microscopy" (Year: 2009).*
(Continued)

Primary Examiner — Blaine Lankford
Assistant Examiner — Lauren K Van Buren
(74) Attorney, Agent, or Firm — McNeill Baur PLLC

(57) ABSTRACT

Uncultured amniotic cell and protein fraction products derived from amniotic fluid and methods of preparing and using those compositions are provided. According to the methods of the present invention, uncultured amniotic cell and protein products may be derived from a large sample of amniotic fluid to provide a higher concentration of tissue regeneration components. Described are methods for separating uncultured amniotic cells or protein fractions from other components of amniotic fluid and the resulting uncultured amniotic cell and protein products. Furthermore, the present invention includes methods for delivering the uncultured amniotic cell and protein products to the skin and eye, including before, during, or after a treatment procedure.

33 Claims, 2 Drawing Sheets

(51) Int. Cl.

| | |
|---|---|
| *C12N 5/073* | (2010.01) |
| *C07K 14/435* | (2006.01) |
| *A61Q 19/08* | (2006.01) |
| *A61K 9/00* | (2006.01) |
| *A61Q 19/00* | (2006.01) |
| *A61K 31/728* | (2006.01) |

(52) U.S. Cl.
CPC .......... *A61K 9/0019* (2013.01); *A61K 9/0021* (2013.01); *A61K 9/0048* (2013.01); *A61K 9/0085* (2013.01); *A61K 31/728* (2013.01); *A61Q 19/004* (2013.01); *A61Q 19/08* (2013.01); *C07K 14/435* (2013.01); *C12N 5/0605* (2013.01); *A61K 2800/91* (2013.01)

(56) References Cited

U.S. PATENT DOCUMENTS

| | | | |
|---|---|---|---|
| 8,021,876 | B2 | 9/2011 | Atala et al. |
| 8,376,984 | B2 | 2/2013 | James |
| 8,586,540 | B2 | 11/2013 | You et al. |
| 8,940,294 | B2 | 1/2015 | Tseng et al. |
| 2005/0054093 | A1 | 3/2005 | Haas |
| 2005/0124003 | A1* | 6/2005 | Atala .................. A61P 25/00 435/7.2 |
| 2007/0073217 | A1 | 3/2007 | James |
| 2008/0227208 | A1* | 9/2008 | Yee .................... G01N 33/72 436/66 |
| 2008/0286378 | A1 | 11/2008 | Behrens et al. |
| 2009/0055099 | A1 | 2/2009 | Rosenfeld et al. |
| 2009/0142835 | A1 | 6/2009 | Kobayashi et al. |
| 2012/0276215 | A1* | 11/2012 | Riordan ................ A61P 1/04 424/583 |
| 2013/0218274 | A1 | 8/2013 | Spencer et al. |
| 2014/0050705 | A1* | 2/2014 | Lim .................. A61K 9/0019 424/93.7 |
| 2014/0141505 | A1 | 5/2014 | Kobayashi et al. |
| 2014/0147511 | A1* | 5/2014 | Tseng .................. A61K 35/51 424/583 |
| 2014/0335046 | A1 | 11/2014 | Matheny |
| 2014/0336600 | A1* | 11/2014 | Harrell ............... A61B 10/0048 604/319 |
| 2014/0348940 | A1 | 11/2014 | Murphy et al. |
| 2015/0025366 | A1 | 1/2015 | Harrell |
| 2015/0140114 | A1 | 5/2015 | Sasko |

OTHER PUBLICATIONS

Bollini et al. "Regenerative Role of the Fetal and Adult Stem Cell Secretone" J. Clin. Med, 2013, 2, 302-327 (Year: 2013).*
Mattson et al. "Graft Failure after Allogenic Hematopoietic Cell Transplantation" Biology of Blood and Marrow Tansplantation, 14: 165-170 (Year: 2008).*
Zawada et al. "Quantitative determination of urea concentrations in cell culture medium" Biochem Cell Biol 2009, Jun. 87(3): 541-544 (Year: 2009).*
VEGF fact sheet (Year: 2021).*
Bajek et al., "Human amniotic-fluid-derived stem cells: a unique source for regenerative medicine," Expert Opin. Biol. Ther. (2014) 14(6), pp. 831-839.
Dasgupta et al., "Amniotic fluid: Source of trophic factors for the developing intestine," World J Gastrointest Pathophysiol, (7)1:38-47, 2016.
De Coppi et al., "Isolation of amniotic stem cell lines with potential for therapy," Nature Biotechnology, vol. 25, No. 1, pp. 100-106, 2007.
Gianazza et al., "Mapping the 5-50-kDa fraction of human amniotic fluid proteins by 2-DE and ESI-MS," Proteomics Clin. Appl. 2007, 1, 167-175.
Good et al., "Amniotic fluid inhibits Toll-like receptor 4 signaling in the fetal and neonatal intestinal epithelium," PNAS, vol. 109, No. 28, pp. 11330-11335, 2012.

International Search Report and Written Opinion of corresponding International Application No. PCT/US2016/039668, dated Sep. 16, 2016 (14 pages).
Maheshwari et al., "TGF-β2 Suppresses Macrophage Cytokine Production and Mucosal Inflammatory Responses in the Developing Intestine," Gastroenterology. 140(1): 242-253, 2011.
Michaels et al., "Comprehensive Proteomic Analysis of the Human Amniotic Fluid Proteome: Gestational Age-Dependent Changes," Journal of Proteome Research, 2007, 6, 1277-1285; Supplemental Table 1 (7 pages) Supplemental Table 2 (1 page).
Phermthai et al., "A novel method to derive amniotic fluid stem cells for therapeutic purposes," BMC Cell Biology, 11:79, doi: 10.1186/1471-2121-11-79., pp. 1-9 (2010).
Roubelakis et al., "In vitro and in vivo properties of distinct populations of amniotic fluid mesenchymal progenitor cells," J. Cell. Mol. Med. vol. 15, No. 9, 2011 pp. 1896-1913.
Savickiene et al., "Human Amniotic Fluid Mesenchymal Stem Cells from Second- and Third-Trimester Amniocentesis: Differentiation Potential, Molecular Signature, and Proteome Analysis," Stem Cells Int. Article ID 319238, 15 pages, 2015.
Sun et al., "Amniotic fluid stem cells provide considerable advantages in epidermal regeneration: B7H4 creates a moderate inflammation microenvironment to promote wound repair," Sci. Rep. 5, 11560; doi: 10.1038/srep11560 (2015).
Sundberg et al., "Filtration and Recirculation of Early Amniotic Fluid. Evaluation of Cell Cultures from 100 Diagnostic Cases," Prenatal Diagnosis, vol. 13, pp. 1101-1110 (1993).
Pieternella, "Amniotic fluid as a novel source of mesenchymal stem cells for therapeutic transplantation," Blood, vol. 102, No. 4, pp. 1548-1549, 2003.
Tong et al., "Potential Function of Amniotic Fluid in Fetal Development-Novel Insights by Comparing the Composition of Human Amniotic Fluid with Umbilical Cord and Maternal Serum at Mid and Late Gestation," J Chin Med Assoc, vol. 72, No. 7, pp. 368-373, Jul. 2009.
Van Opstal et al., "Follow-up investigations in uncultured amniotic fluid cells after uncertain cytogenetic results," Prenatal Diagnosis; vol. 21, pp. 75-80 (2001).
"Clinical Overview and Description of Amniotic Fluid and OrthoFlo," MiMedx; 4 pages.
"MiMedx Third Quarter Record Revenue is $49 Million," Press Release; 4 pages, Oct. 12, 2015.
"MiMedx Announces Nationwide Launch of New Ambient Temperature Version of OrthoFlo," Press Release; 4 pages, Jul. 25, 2016.
"OrthoFlo—An Amniotic Fluid Derived Allograft for Homologous Use," MiMedx Brochure; 2 pages; 2015.
"OrthoFlo—Scientific & Clinical Monograph," MiMedx brochure; 24 pages; 2017.
Amniovisc Brochure, Liventa Bioscience, 2 pages; 2014.
Bhattacharya, "Clinical Use of Amniotic Fluid in Osteoarthritis: A Source of Cell Therapy," Chapter 38 in Regenerative Medicine Using Pregnancy-Specific Biological Substances, pp. 395-403, Eds. Bhattacharya and Stubblefield, Springer-Verlag London Ltd, 2011.
Buhimschi et al., "Proteomic Biomarkers of Intra-amniotic Inflammation: Relationship with Funisitis and Early-onset Sepsis in the Premature Neonate," Pediatric Research, vol. 61, No. 3, pp. 318-324; 2007.
Buhimschi et al., "Proteomic Profiling of the Amniotic Fluid to Detect Inflammation, Infection, and Neonatal Sepsis," PLOS Medicine, vol. 4, Issue 1, e18, pp. 84-94, 2007.
Bujold et al., "Proteomic profiling of amniotic fluid in premature labor using two-dimensional liquid separation and mass spectrometry," J. Matern Fetal Neonatal Med., 21(10):697-713; 2008.
Demesmin et al., "Amniotic Fluid as a Homologue to Synovial Fluid: Interim Analysis of Prospective, Multi-Center Dutcome Observational Cohort Registry of Amniotic Fluid Treatment for Osteoarthritis of the Knee," AAPM 2015 Annual Meeting Late-Breaking Abstracts vol. 16, No. 3; Abstract LB004; 2015.
Kim et al., "Human amniotic fluid-derived stem cells have characteristics of multipotent stem cells," Cell Prolif. (40)1: 75-90, 2007.
Oh et al., "Proteomic Biomarkers in Second Trimester Amniotic Fluid That Identify Women Who Are Destined to Develop Preeclampsia," Reproductive Sciences, 19(7): 694-703, 2012.

(56) References Cited

OTHER PUBLICATIONS

Tseng et al., "Amniotic Membrane Transplantation With or Without Limbal Allografts for Corneal Surface Reconstruction in Patients With Limbal Stem Cell Deficiency," Arch Opthalmol, vol. 116, pp. 431-441, 1998.
Tsubota et al., "Surgical Reconstruction of the Ocular Surface in Advanced Ocular Cicatricial Pemphigoid and Stevens-Johnson Syndrome," Am J Opthalmol. 122(1):38-52; 1996.
Uchida et al., "Neurotrophic Function of Conditioned Medium From Human Amniotic Epithelial Cells," J Neurosci Res. 62(4):585-590; 2000.
Woo et al., "Effects of amniotic membrane on epithelial wound healing and stromal remodelling after excimer laser keratectomy in rabbit cornea," Br J Ophthalmol. 85(3):345-349; 2001.
Giorlandino et al., "Blood Contamination of Amniotic Fluid Amniocentesis in Relation to Placental Location," Prenatal Diagnosis 16(2): 180-182, 1996.
Jiang and Zhang, "Differentiation of Cardiomyocytes from Amniotic Fluid-Derived Mesenchymal Stem Cells by Combined Induction with Transforming Growth Factor β1 and 5-Azacytidine," Molecular Medicine Reports, 16 (5):5887-5893, 2017.
Ponder, "The Measurement of the Diameter of Erythrocytes V. The Relation of the Diameter to the Thickness," Experimental Physiology, 20:29-39, 1930.
Amersham Biosciences, Ficoll-Paque PLUS, For in vitro isolation of lymphocytes, 18-1152-69, Edition AB (2001) (20 pages).
GE Healthcare Life Sciences, Instructions 28-4039-56AD, Ficoll-PaqueTM PREMIUM, Ficoll-Paque PREMIUM 1.084, Ficoll-Paque PREMIUM 1.073 Cell Preparation Media (2005-2013) (16 pages).
Gordon et al., "Recovery of Human Mesenchymal Stem Cells Following Dehydration and Rehydration," Cryobiology 43, 182-187 (2001).
Natan et al., "Freeze-Drying of Mononuclear Cells Derived from Umbilical Cord Blood Followed by Colony Formation," PLOS One, 4(4):e5240 (2009).
Amersham Biosciences, Percoll, Methodology and Applications, 18-1115-69, Edition AC (2001) (84 pages).
Sigma-Aldrich, Product Information for Percoll and Percoll PLUS (2015) (4 pages).
U.S. Department of Health and Human Services, Food and Drug Administration, "Regulatory Considerations for Human Cells, Tissues, and Cellular and Tissue-Based Products: Minimal Manipulation and Homologous Use. Guidance for Industry and Food and Drug Administration Staff," (2017) (28 pages).
Cremer et al., "Characterization of Cells of Amniotic Fluids by Immunological Identification of Intermediate-Sized Filaments: Presence of Cells of Different Tissue Origin," Hum Genet (1981) 59:373-379.
De Coppi at al., "Stem cells derived from amniotic fluid: new potentials in regenerative medicine," Reproductive BioMedicine Online (2009) vol. 18 Suppl. 1, pp. 17-27.
Gosden et al., "Amniotic Fluid Cell Types and Culture," British Medical Bulletin (1983) vol. 39, No. 4, pp. 348-354.
Hibino et al., "Comparison of Human Bone Marrow Mononuclear Cell Isolation Methods for Creating Tissue-Engineered Vascular Grafts: Novel Filter System Versus Traditional Density Centrifugation Method," Tissue Engineering: Part C, vol. 17, No. 10, pp. 993-998, 2011.
Kaneka, Product sheet for Bone Marrow MSC Separation Device, 2 pages, 2013.
Ogston et al., "Degradation of the Hyaluronic acid Complex of Synovial Fluid by Proteolytic Enzymes and by Ethylenediaminetetraacetic acid," Biochem J. 72(2):301-305, 1959.

Otsuru et al., "Improved isolation and expansion of bone marrow mesenchymal stromal cells using a novel marrow filter device," Cytotherapy, 2013; 15: pp. 46-153.
Perluigi et al., "Proteomic analysis for the study of amniotic fluid protein composition," Journal of Prenatal Medicine, 2009; 3 (3): 39-41.
Pipino et al., "Molecular and Phenotypic Characterization of Human Amniotic Fluid-Derived Cells: A Morphological and Proteomic Approach," Stem Cells and Development, Published Online: Jan. 21, 2015, https://doi.org/10.1089/scd.2014.0453, pp. 1-14.
Purecell™ Select System for Whole Blood MNC Enrichment, description printed Jun. 17, 2015 (5 pages).
Roubelakis et al., Molecular and Proteomic Characterization of Human Mesenchymal Stem Cells Derived from Amniotic Fluid: Comparison to Bone Marrow Mesenchymal Stem Cells, Stem Cells and Development 16:931-951 (2007).
Underwood et al., "Amniotic Fluid: Not Just Fetal Urine Anymore," Journal of Perinatology, 2005, 25:341-348.
Wagner et al., "Monocyte enrichment of mononuclear apheresis preparations with a multistep back-flush procedure an a cord blood filter," Transfusion, 2005; 45:433-439.
Yasutake et al., "Stem cell collection filter system for human placental/umbilical cord blood processing," Vox Sanguinis (2001) 80, pp. 101-105.
Chen et al., "Variations of Protein Levels in Human Amniotic Fluid Stem Cells CD 117/2 Over Passages 5-25", Journal of Proteome Research, 8, pp. 5285-5295 (2009).
Cowman et al., "The content and size of hyaluronan in biological fluids and tissues", Frontiers in Immunology, vol. 6, Article 261, pp. 1-8 (Jun. 6, 2015).
Ditadi et al., "Human and murine amniotic fluid c-Kit+Lin-cells display hematopoietic activity", Blood, 113(17); pp. 3953-3960 (Apr. 23, 2009).
Hoehn et al., Cultivated Cells from Diagnostic Amniocentesis in Second Trimester Pregnancies. I. Clonal Morphology and Growth Potential, Pediatric Research, 8: 746-754 (1974).
Pierce et al., Collection and characterization of amniotic fluid from scheduled C-section deliveries, Cell Tissue Bank DOI 10.1007/S10561-016-9572-7 (2016).
Rennie et al., Applications of Amniotic Membrane and Fluid in Stem Cell Biology and Regenerative Medicine, Stem Cells International, vol. 2012, Article ID 721538, 13 pages, doi:10.1155/2012/721538.
Roubelakis et al., Amniotic Fluid and Amniotic Membrane Stem Cells: Marker Discovery, Stem Cells International, vol. 2012, Article ID 107836, 9 pages, doi:10.1155/2012/107836.
Roy et al., "Intermediate layer contribution in placental membrane allografts", J. Tissue Eng Regen Med., pp. 1-10 (2020), with supplemental figure 1.
"Efficacy of Dehydrated Cell and Protein Concentrate Versus Corticosteroid", ClinicalTrials.gov, Identifier: NCT03710005 (2018) (7 pages).
StimLabs, Ascent™ Dehydrated Amitotic Fluid Allograft Brochure (2017) (2 pages).
RayBio® Human Hemoglobin ELISA Kit, RayBiotech, Catalog #: ELH-Hgb, User Manual, Last revised Dec. 7, 2015 (12 pages).
RayBio® Human Hemoglobin ELISA Kit, RayBiotech, Catalog #: ELH-Hgb, User Manual, Last revised Jan. 29, 2021 (12 pages).
RayBio® Human Hemoglobin ELISA Kit, RayBiotech, Catalog #: ELH-Hgb, User Manual, Last revised Jul. 6, 2017 (12 pages).
RayBio® Human Hemoglobin ELISA Kit, RayBiotech, Catalog #: ELH-Hgb, User Manual, Last revised Jun. 14, 2021 (12 pages).

\* cited by examiner

PRODUCTS DERIVED FROM AMNIOTIC FLUID AND METHODS OF USE

CROSS REFERENCE TO RELATED APPLICATIONS

This application is a national phase entry pursuant to 35 U.S.C. § 371 of International Application No. PCT/US2016/039668, filed Jun. 27, 2016, which claims the benefit of priority of U.S. Provisional Application No. 62/185,605, filed Jun. 27, 2015, each of which is incorporated by reference herein in its entirety for any purpose.

FIELD

This application relates to compositions derived from amniotic fluid and methods of preparing and using those compositions.

INTRODUCTION AND SUMMARY

Amniotic fluid contains stem cells, which can differentiate into several tissues when subjected to specific conditions. Undifferentiated stem cells are important therapeutics for regenerative medicine and wound healing. In addition to stem cells, amniotic fluid also contains other cell types (including blood cells and other differentiated cells), proteins, peptides, electrolytes, and small organic molecules (such as urea), some of which may or may not be important for tissue regeneration and wound healing.

Current methods of preparing uncultured amniotic cell products from amniotic fluid involve centrifuging the fluid and resuspending the resulting pellet in a medium. However, the resuspended pellet contains blood cells, cellular debris, and other components that may be disfavored for therapeutic applications. In contrast, embodiments of the present invention include uncultured amniotic cell products substantially free of one or more of blood cells, red blood cells, white blood cells, urea, electrolytes, amino acids, or peptides consisting of 2 amino acids. Uncultured amniotic cell products may be preserved and a population of those cells may still be viable. Furthermore, unlike centrifugation methods, some methods of the present invention may result in separation of adherent amniotic cells, including stem cells, from non-adherent cells, such as blood cells.

Current methods of preparing cultured amniotic cell products involves culturing to expand one or more populations of cells, such as plastic-adherent amniotic cells. Other methods further involve selecting cells expressing specific cell-surface ligands after expansion in culture (see U.S. Pat. Nos. 8,021,876, 8,940,294, 8,586,540, and Roubelakis, M. G., et al., (2007), *Stem Cells Der* 16(6): 931-952). Unlike the methods of the present invention, preparing cultured amniotic cell products is costly and time consuming. In addition, when amniotic cells are cultured, some populations of cells may divide more slowly than other populations. This may lead to cultured amniotic cell products containing a lower number of or lower concentration of some amniotic cell populations. In contrast, embodiments of uncultured amniotic cell products of the invention may include broader populations of amniotic cells, including a greater selection of stem cells.

Cell-separation filters have been specifically developed and used with small volumes of whole blood, bone marrow, and umbilical cord blood. See Hibino, N., et al., (2011), *Tissue Eng Part C Methods* 17(10): 993-998 and U.S. 2009/0142835. For example, retrieval of total cord blood is about 60 mL, donation of about 1 unit of fresh human blood is equivalent to about 450 mL, and retrieval of bone marrow aspirate from a single donor is limited to about 30-40 mL. The largest source of fluid containing stem cells that can be removed from a human without injuring the human is believed to be amniotic fluid, which totals up to about 1 L. Unlike known methods, methods of the present invention may be used to isolate amniotic cells from small volumes of amniotic fluid (e.g., an amniocentesis sample) as well as larger volumes (e.g., collected from C-section).

Amniotic fluid also contains a multitude of proteins that may be important for regenerative medicine and wound healing. Protein fractions derived from amniotic fluid or combination products comprising uncultured amniotic cells and protein fractions would also be advantageous for their tissue regeneration and wound healing potential. Embodiments of the present invention include protein fractions or combination products derived from amniotic fluid that are substantially free of one or more of blood cells, red blood cells, white blood cells, urea, electrolytes, amino acids, or peptides consisting of 2 amino acids.

In addition, cost effective and efficient methods of preparing uncultured amniotic cell products, protein fraction products, or combination products from a large volume of amniotic fluid obtained from a donor undergoing a Cesarean section (C-section) would also be advantageous. Advantages of the present invention include the minimal number of processing steps involved and the scalability of the methods to process large volumes of amniotic fluid.

The use of unprocessed amniotic fluid and amniotic membrane materials to treat the skin following a skin treatment procedure has been described. See US 2015/0140114. In contrast to using unprocessed amniotic fluid, therapeutic uses of amniotic cell products and protein fraction products derived from a large sample of amniotic fluid according to some embodiments of the present invention may provide a higher concentration of amniotic cells, proteins, or other tissue regeneration components. Furthermore, embodiments of the present invention include methods for delivering uncultured amniotic cell products or protein fraction products to the skin, an eye, a joint, or the spine. The products may be delivered before, during, or after a medical procedure directly to the area being treated where tissue regeneration and healing may be needed the most.

Provided herein is a product derived from a sample of amniotic fluid comprising a population of uncultured amniotic cells, wherein the product is substantially free of red blood cells.

Also provided herein is a product derived from a sample of amniotic fluid comprising a protein fraction, wherein the product is substantially free of urea.

Also provided herein is a product comprising a first product derived from a sample of amniotic fluid comprising a population of uncultured amniotic cells, wherein the product is substantially free of red blood cells; and a second product derived from a sample of amniotic fluid comprising a protein fraction, wherein the product is substantially free of urea.

In some embodiments, the product is substantially free of one or more of blood cells, red blood cells, white blood cells, urea, electrolytes, amino acids, or peptides consisting of 2 amino acids.

In some embodiments, the product comprises amniotic stem cells. In some embodiments, the product comprises adherent cells. In some embodiments, the product comprises c-kit positive cells. In some embodiments, the product comprises hematopoietic progenitor cells, mesenchymal stem cells, embryonic stem cells, epithelial cells, fibroblast cells, muscle cells, or nerve cells.

In some embodiments, the product comprises a total cell count of less than a value, of greater than a value, of at least a value, of a value, or ranging from any two values, wherein the value is selected from about $1 \times 10^2$, about $2 \times 10^2$, about $3 \times 10^2$, about $4 \times 10^2$, about $5 \times 10^2$, about $6 \times 10^2$, about $7 \times 10^2$, about $8 \times 10^2$, about $9 \times 10^2$, about $1 \times 10^3$, about $2 \times 10^3$, about $3 \times 10^3$, about $4 \times 10^3$, about $5 \times 10^3$, about $6 \times 10^3$, about $7 \times 10^3$, about $8 \times 10^3$, about $9 \times 10^3$, about $1 \times 10^4$ cells, about $2 \times 10^4$ cells, about $3 \times 10^4$ cells, about $4 \times 10^4$ cells, about $5 \times 10^4$ cells, about $6 \times 10^4$ cells, about $7 \times 10^4$ cells, about $8 \times 10^4$ cells, about $9 \times 10^4$ cells, about $1 \times 10^5$ cells, about $2 \times 10^5$ cells, about $3 \times 10^5$ cells, about $4 \times 10^5$ cells, about $5 \times 10^5$ cells, about $6 \times 10^5$ cells, about $7 \times 10^5$ cells, about $8 \times 10^5$ cells, about $9 \times 10^5$ cells, about $1 \times 10^6$ cells, about $2 \times 10^6$ cells, about $3 \times 10^6$ cells, about $4 \times 10^6$ cells, about $5 \times 10^6$ cells, about $6 \times 10^6$ cells, about $7 \times 10^6$ cells, about $8 \times 10^6$ cells, about $9 \times 10^6$ cells, about $1 \times 10^7$ cells, about $2 \times 10^7$ cells, about $3 \times 10^7$ cells, about $4 \times 10^7$ cells, about $5 \times 10^7$ cells, about $6 \times 10^7$ cells, about $7 \times 10^7$ cells, about $8 \times 10^7$ cells, about $9 \times 10^7$ cells, about $1 \times 10^8$ cells, about $2 \times 10^8$ cells, about $3 \times 10^8$ cells, about $4 \times 10^8$ cells, about $5 \times 10^8$ cells, about $6 \times 10^8$ cells, about $7 \times 10^8$ cells, about $8 \times 10^8$ cells, about $9 \times 10^8$ cells, and about $1 \times 10^9$ cells.

In some embodiments, the product has a total protein content of less than a value, of greater than a value, of at least a value, or ranging from any two values, wherein the value is selected from about 1 µg, about 5 µg, about 10 µg, about 20 µg, about 25 µg, about 30 µg, about 40 µg, about 50 µg, about 60 µg, about 70 µg, about 75 µg, about 80 µg, about 90 µg, about 100 µg, about 125 µg, about 150 µg, about 175 µg, about 200 µg, about 225 µg, about 250 µg, about 275 g, about 300 µg, about 325 µg, about 350 µg, about 375 µg, about 400 µg, about 425 µg, about 450 µg, about 475 µg, about 500 µg, about 525 µg, about 550 µg, about 575 µg, about 600 µg, about 625 µg, about 650 µg, about 675 µg, about 700 µg, about 750 µg, about 800 µg, about 850 µg, about 900 µg, about 950 µg, about 1 mg, about 5 mg, about 10 mg, about 20 mg, about 25 mg, about 30 mg, about 40 mg, about 50 mg, about 60 mg, about 70 mg, about 75 mg, about 80 mg, about 90 mg, and about 100 mg.

In some embodiments, the product has a total protein content per mass of product of less than a value, of greater than a value, of at least a value, or ranging from any two values, wherein the value is selected from about 1 µg/mg, about 5 µg/mg, about 10 µg/mg, about 15 µg/mg, about 20 µg/mg, about 25 µg/mg, about 30 µg/mg, about 35 µg/mg, about 40 µg/mg, about 45 µg/mg, about 50 µg/mg, about 55 µg/mg, about 60 µg/mg, about 65 µg/mg, about 70 µg/mg, about 75 µg/mg, about 80 µg/mg, about 85 µg/mg, about 90 µg/mg, about 95 µg/mg, about 100 µg/mg, about 110 µg/mg, about 120 µg/mg, about 130 µg/mg, about 140 µg/mg, about 150 µg/mg, about 160 µg/mg, about 170 µg/mg, about 180 µg/mg, about 190 µg/mg, about 200 µg/mg, about 210 µg/mg, about 220 µg/mg, about 230 µg/mg, about 240 µg/mg, about 250 µg/mg, about 260 µg/mg, about 270 µg/mg, about 280 µg/mg, about 290 µg/mg, about 300 µg/mg.

In some embodiments, the product has a total protein content per volume of product of less than a value, of greater than a value, of at least a value, or ranging from any two values, wherein the value is selected from about 1 µg/mL, about 5 µg/mL, about 10 µg/mL, about 15 µg/mL, about 25 µg/mL, about 30 µg/mL, about 40 µg/mL, about 50 µg/mL, about 60 µg/mL, about 70 µg/mL, about 75 µg/mL, about 80 µg/mL, about 90 µg/mL, about 100 µg/mL, about 125 µg/mL, about 150 µg/mL, about 175 µg/mL, about 200 µg/mL, about 225 µg/mL, about 250 µg/mL, about 275 µg/mL, about 300 µg/mL, about 350 µg/mL, about 400 µg/mL, about 450 µg/mL, about 500 µg/mL, about 600 µg/mL, about 700 µg/mL, about 800 µg/mL, about 900 µg/mL, about 1 mg/mL, about 2 mg/mL, about 3 mg/mL, about 4 mg/mL, about 5 mg/mL, about 6 mg/mL, about 7 mg/mL, about 8 mg/mL, about 9 mg/mL, about 10 mg/mL, about 11 mg/mL, about 12 mg/mL, about 13 mg/mL, about 14 mg/mL, and about 15 mg/mL.

In some embodiments, the product comprises proteins having a molecular weight of less than a value, of greater than a value, of at least a value, of a value, or ranging from any two values, wherein the value is selected from about 1 kDa, about 2 kDa, about 5 kDa, about 10 kDa, about 20 kDa, about 30 kDa, about 40 kDa, about 50 kDa, about 60 kDa, about 70 kDa, about 80 kDa, about 90 kDa, about 100 kDa, about 120 kDa, about 140 kDa, about 160 kDa, about 180 kDa, about 200 kDa, about 220 kDa, about 240 kDa, about 260 kDa, about 280 kDa, about 300 kDa, about 350 kDa, about 400 kDa, about 450 kDa, about 500 kDa, about 550 kDa, and about 600 kDa.

In some embodiments, the product comprises growth factors, glycoproteins, glycosaminoglycans (GAGs), poly-carbohydrates, or cytokines.

In some embodiments, the product comprises epidermal growth factor (EGF), transforming growth factor alpha (TGFa), transforming growth factor beta (TGFβ), insulin-like growth factor I (IGF-I), insulin-like growth factor II (IGF-II), erythropoietin (EPO), granulocyte colony-stimulating factor (G-CSF), a tissue inhibitor of metallopeptidase (TIMP), lactoferrin (LF), alpha defensin 1 (HNP1), alpha defensing 2 (HPN2), alpha defensing 3 (HPN3), interleukin 1A receptor (IL-1Ra), or hyaluronic acid.

In some embodiments, the hemoglobin content of the product is not detectable.

In some embodiments, the product has a hemoglobin content of less than a value, of greater than a value, of at least a value, of a value, or ranging from any two values, wherein the value is selected from about 3 mg, about 2 mg, about 1 mg, about 900 µg, about 800 µg, about 700 µg, about 600 µg, about 500 µg, about 400 µg, about 300 µg, about 200 µg, about 100 µg, about 50 µg, about 40 µg, about 30 µg, about 20 µg, about 10 µg, about 9 µg, about 8 µg, about 7 µg, about 6 µg, about 5 µg, about 4 µg, about 3 µg, about 2 µg, about 1 µg, about 0.9 µg, about 0.8 µg, about 0.7 µg, about 0.6 µg, about 0.5 µg, about 0.4 µg, about 0.3 µg, about 0.2 µg, about 0.1 µg, about 0.09 µg, about 0.08 µg, about 0.07 µg, about 0.06 µg, about 0.05 µg, about 0.04 µg, about 0.03 µg, about 0.02 µg, and about 0.01 µg.

In some embodiments, the product has a hemoglobin content per dry mass of the product of less than a value, of greater than a value, of at least a value, of a value, or ranging from any two values, wherein the value is selected from about 10 µg/mg, about 9 µg/mg, about 8 µg/mg, about 7 µg/mg, about 6 µg/mg, about 5 µg/mg, about 4 µg/mg, about 3 µg/mg, about 2 µg/mg, about 1 µg/mg, about 0.9 µg/mg, about 0.8 µg/mg, about 0.7 µg/mg, about 0.6 µg/mg, about 0.5 µg/mg, about 0.4 µg/mg, about 0.3 µg/mg, about 0.2 µg/mg, about 0.1 µg/mg, about 0.09 µg/mg, about 0.08 µg/mg, about 0.07 µg/mg, about 0.06 µg/mg, about 0.05 µg/mg, about 0.04 µg/mg, about 0.03 µg/mg, about 0.02 µg/mg, and about 0.01 µg/mg.

In some embodiments, the product has a hemoglobin content per volume of the product of less than a value, of greater than a value, of at least a value, of a value, or ranging from any two values, wherein the value is selected from about 10 µg/mL, about 9 µg/mL, about 8 µg/mL, about 7 µg/mL, about 6 µg/mL, about 5 µg/mL, about 4 µg/mL, about 3 µg/mL, about 2 µg/mL, about 1 µg/mL, about 0.9 µg/mL, about 0.8 µg/mL, about 0.7 µg/mL, about 0.6 µg/mL, about 0.5 µg/mL, about 0.4 µg/mL, about 0.3 µg/mL, about 0.2 µg/mL, about 0.1 µg/mL, about 0.09 µg/mL, about 0.08 µg/mL, about 0.07 gig/mL, about 0.06 µg/mL, about 0.05 µg/mL, about 0.04 µg/mL, about 0.03 µg/mL, about 0.02 µg/mL, and about 0.01 µg/mL.

In some embodiments, the urea or electrolyte content of the product is not detectable.

In some embodiments, the product has a urea content of less than a value, of greater than a value, of at least a value, of a value, or ranging from any two values, wherein the value is selected from about 300 µg, about 250 µg, about 200 µg, about 150 µg, about 100 µg, about 90 µg, about 80 µg, about 70 µg, about 60 µg, about 50 µg, about 40 µg, about 30 µg, about 20 µg, about 10 µg, about 9 µg, about 8 µg, about 7 µg, about 6 µg, about 5 µg, about 4 µg, about 3 µg, about 2 µg, about 1 µg, about 0.9 µg, about 0.8 µg, about 0.7 µg, about 0.6 µg, about 0.5 µg, about 0.4 µg, about 0.3 µg, about 0.2 µg, about 0.1 µg, about 0.09 µg, about 0.08 µg, about 0.07 µg, about 0.06 µg, about 0.05 µg, about 0.04 µg, about 0.03 µg, about 0.02 µg, and about 0.01 µg.

In some embodiments, the product has a urea content per mass of product of less than a value, of greater than a value, of at least a value, of a value, or ranging from any two values, wherein the value is selected from about 100 µg/mg, about 90 µg/mg, about 80 µg/mg, about 70 µg/mg, about 60 µg/mg, about 50 µg/mg, about 40 µg/mg, about 30 µg/mg, about 20 µg/mg, about 10 µg/mg, about 9 µg/mg, about 8 µg/mg, about 7 µg/mg, about 6 µg/mg, about 5 µg/mg, about 4 µg/mg, about 3 µg/mg, about 2 µg/mg, about 1 µg/mg, about 0.9 µg/mg, about 0.8 µg/mg, about 0.7 µg/mg, about 0.6 µg/mg, about 0.5 µg/mg, about 0.4 µg/mg, about 0.3 µg/mg, about 0.2 µg/mg, about 0.1 µg/mg, about 0.09 µg/mg, about 0.08 µg/mg, about 0.07 µg/mg, about 0.06 µg/mg, about 0.05 µg/mg, about 0.04 µg/mg, about 0.03 µg/mg, about 0.02 µg/mg, and about 0.01 µg/mg.

In some embodiments, the product has a urea content per volume of product of less than a value, of greater than a value, of at least a value, of a value, or ranging from any two values, wherein the value is selected from about 100 µg/mL, about 90 µg/mL, about 80 µg/mL, about 70 µg/mL, about 60 µg/mL, about 50 µg/mL, about 40 µg/mL, about 30 µg/mL, about 20 µg/mL, about 10 µg/mL, about 9 µg/mL, about 8 µg/mL, about 7 µg/mL, about 6 µg/mL, about 5 µg/mL, about 4 µg/mL, about 3 µg/mL, about 2 µg/mL, about 1 µg/mL, about 0.9 µg/mL, about 0.8 µg/mL, about 0.7 µg/mL, about 0.6 µg/mL, about 0.5 µg/mL, about 0.4 µg/mL, about 0.3 µg/mL, about 0.2 µg/mL, about 0.1 µg/mL, about 0.09 µg/mL, about 0.08 µg/mL, about 0.07 µg/mL, about 0.06 µg/mL, about 0.05 µg/mL, about 0.04 µg/mL, about 0.03 µg/mL, about 0.02 µg/mL, and about 0.01 µg/mL.

In some embodiments, the sample of amniotic fluid is from a human donor. In some embodiments, the sample of amniotic fluid is from a single donor. In some embodiments, the sample of amniotic fluid is from multiple donors. In some embodiments, the serum of the donor of the sample of amniotic fluid is negative for one or more of antibodies to HIV-1, antibodies to HIV-2, antibodies to HBV, antibodies to HCV, antibodies to HTLV-I, or antibodies to HTLV-II.

In some embodiments, the product is cryopreserved, partially dehydrated, dehydrated, lyophilized, refrigerated, or frozen.

In some embodiments, the product is powderized. In some embodiments, the product has a mean particle size of less than a value, of greater than a value, of at least a value, of a value, or ranging from any two values, wherein the value is selected from about 1 µm, about 5 µm, about 10 µm, about 15 µm, about 20 µm, about 25 µm, about 30 µm, about 35 µm, about 40 µm, about 45 µm, about 50 µm, about 55 µm, about 60 µm, about 65 µm, about 70 µm, about 75 µm, about 80 µm, about 85 µm, about 90 µm, about 95 µm, about 100 µm, about 110 µm, about 120 µm, about 130 µm, about 140 µm, about 150 µm, about 160 µm, about 170 µm, about 180 µm, about 190 µm, about 200 µm, about 210 µm, about 220 µm, about 230 µm, about 240 µm, about 250 µm, about 260 µm, about 270 µm, about 280 µm, about 290 µm, and about 300 µm.

In some embodiments, the product has a residual moisture content of less than a percentage, of greater than a percentage, of at least a percentage, of a percentage, or ranging from any two percentages, wherein the percentage is selected from about 1%, about 2%, about 3%, about 4%, about 5%, about 6%, about 7%, about 8%, about 9%, about 10%, about 11%, about 12%, about 13%, about 14%, and about 15%.

In some embodiments, the product is sterilized.

Also provided herein is a method of preparing a population of uncultured amniotic cells derived from a sample of amniotic fluid comprising: filtering the sample of amniotic fluid through a cell-separation filter; and collecting the population of cells retained by the cell-separation filter.

In some embodiments, the population of cells is substantially free of one or more of blood cells, red blood cells, white blood cells, urea, electrolytes, amino acids, or peptides consisting of 2 amino acids.

In some embodiments, the population of cells is collected in a cell collection medium. In some embodiments, the cell collection medium comprises a protease, a protease inhibitor, a polysaccharide, or a cryoprotectant. In some embodiments, the protease is trypsin, chymotrypsin, or papain.

In some embodiments, the population of cells is collected by flushing, enzymatically removing, or scraping the cells from the cell-separation filter.

In some embodiments, the method further comprises pelleting cells of the sample of amniotic fluid, resuspending the pelleted cells in a fluid, and filtering the resuspended cells as the sample of amniotic fluid.

In some embodiments, the method further comprises fractionating the population of cells.

Also provided herein is a method of preparing at least one protein fraction derived from a sample of amniotic fluid comprising: filtering the sample of amniotic fluid through a cell-separation filter; and fractionating the filtrate into at least one protein fraction. Also provided herein is a method of preparing at least one protein fraction derived from a sample of amniotic fluid comprising: pelleting cells of the sample of amniotic fluid; and fractionating the supernatant into at least one protein fraction under non-reducing conditions. In some embodiments, the protein fraction is substantially free of one or more of blood cells, red blood cells, white blood cells, urea, electrolytes, amino acids, or peptides consisting of 2 amino acids.

In some embodiments, a method disclosed herein further comprises removing debris from the sample of amniotic fluid before filtering the sample through the cell-separation filter or before pelleting cells of the sample of amniotic fluid. In some embodiments, the method further comprises removing cells or debris from the cell-separation filtrate or from the protein fraction. In some embodiments, the method further comprises lysing cells in the cell-separation filtrate, in the population of cells, in the fractionated population of cells, or in the protein fraction. In some embodiments, the method further comprises removing the debris. In some embodiments, the removing is by filtration or centrifugation. In some embodiments, the removing is by filtration through a polymer filter. In some embodiments, the cell-separation filter is a polymer filter. In some embodiments, the polymer filter is a polypropylene filter, a nylon filter, or a polyester filter.

In some embodiments, the cell-separation filter has a size cut off of less than a value, of greater than a value, of at least a value, of a value, or ranging from any two values, wherein the value is selected from about 3 μm, about 4 μm, about 5 μm, about 6 μm, about 7 μm, about 8 μm, about 9 μm, about 10 μm, about 11 μm, about 12 μm, about 13 μm, about 14 μm, about 15 μm, about 16 μm, about 17 μm, about 18 μm, about 19 μm, about 20 μm, about 21 μm, about 22 μm, about 23 μm, about 24 μm, about 25 μm, about 26 μm, about 27 μm, about 28 μm, about 29 μm, about 30 μm, about 31 μm, about 32 μm and about 33 μm.

In some embodiments, the filtering is in a closed system.

In some embodiments, the fractionating comprises two, at least two, three, at least three, four, at least four, five, or at least five fractionating steps. In some embodiments, the fractionating is by size, density, or affinity. In some embodiments, the fractionating is by filtration, centrifugation, or chromatography. In some embodiments, the chromatography is size-exclusion chromatography, ion-exchange chromatography, or affinity chromatography. In some embodiments, the filtration is size filtration. In some embodiments, the filtration comprises using one, two, three, four, five or more filters. In some embodiments, the filter has a molecular weight cut off of less than a value, of greater than a value, of at least a value, of a value, or ranging from any two values, wherein the value is selected from about 600 kDa, about 500 kDa, about 400 kDa, about 300 kDa, about 200 kDa, 100 kDa, about 50 kDa, about 30 kDa, about 10 kDa, about 5 kDa, about 3 kDa, about 2 kDa, and about 1 kDa.

In some embodiments, the filter has a size cut off of less than a value, of greater than a value, of at least a value, of a value, or ranging from any two values, wherein the value is selected from about 3 μm, about 4 μm, about 5 μm, about 6 μm, about 7 μm, about 8 μm, about 9 μm, about 10 μm, about 11 μm, about 12 μm, about 13 μm, about 14 μm, about 15 μm, about 16 μm, about 17 μm, about 18 μm, about 19 μm, about 20 μm, about 21 μm, about 22 μm, about 23 μm, about 24 μm, about 25 μm, about 26 μm, about 27 μm, about 28 μm, about 29 μm, about 30 μm, about 31 μm, about 32 μm, and about 33 μm.

In some embodiments, the fractionating is by affinity. In some embodiments, the affinity comprises interaction between a receptor and a ligand or between an antigen and an antibody.

In some embodiments, the fractionating reduces the level of one or more of blood cells, red blood cells, white blood cells, urea, electrolytes, amino acids, or peptides consisting of 2 amino acids in the cell-separation filtrate, in the population of cells, in the fractionated population of cells, or in the protein fraction.

In some embodiments, the sample of amniotic fluid is from a human donor. In some embodiments, the sample of amniotic fluid is from a single donor. In some embodiments, the sample of human amniotic fluid is from multiple donors.

In some embodiments, the method further comprises cryopreserving, partially dehydrating, dehydrating, lyophilizing, refrigerating, or freezing the population of cells, the fractionated population of cells, or the protein fraction.

In some embodiments, the method further comprises powderizing the population of collected cells, the fractionated population of collected cells, or the protein fraction.

In some embodiments, the partially dehydrating or dehydrating is by using a dehydration fluid that decreases the water content of the population of collected cells, the fractionated population of collected cells, or the protein fraction. In some embodiments, the dehydration fluid comprises an alcohol, an organic solvent, a hydrophilic polymer, or a salt. In some embodiments, the hydrophilic polymer is polyoxyethylene or a polysaccharide. In some embodiments, the polysaccharide is a cellulose derivative or dextrose.

In some embodiments, the method further comprises combining at least one population of uncultured amniotic cells and at least one protein fraction, combining two or more populations of uncultured amniotic cells, or combining two or more protein fractions. In some embodiments, the combination is derived from amniotic fluid of the same donor.

Also provided is a product prepared according to a method of preparation disclosed herein.

Also provided is a pharmaceutical composition comprising a product disclosed herein and a pharmaceutically acceptable carrier. In some embodiments, the pharmaceutical composition comprises a cream, lotion, emulsion, gel, liposome, nanoparticle, spray, or ointment. Also provided herein is a kit comprising a product disclosed herein and a pharmaceutically acceptable carrier. In some embodiments, the pharmaceutically acceptable carrier comprises a cream, lotion, emulsion, gel, liposome, nanoparticle, spray, or ointment. In some embodiments, the pharmaceutically acceptable carrier comprises water, saline, or artificial tears. In some embodiments, the pharmaceutically acceptable carrier comprises hyaluronic acid. In some embodiments, the pharmaceutically acceptable carrier comprises a bulking agent, protein carrier, a polysaccharide, or a polymer. In some embodiments, the protein carrier comprises collagen, fibronectin, elastin, or laminin. In some embodiments, the polysaccharide is a carboxymethylcellulose a carboxyethylcellulose, a hydroxypropylcellulose, a hydroxyethylcellulose, or chitosan. In some embodiments, the pharmaceutically acceptable carrier comprises polyoxyethylene oxide.

Also provided is a method of treating skin of a subject comprising delivering a product disclosed herein or a pharmaceutical composition disclosed herein to the skin by topical administration. Also provided is a method of treating skin of a subject comprising delivering a product disclosed herein or a pharmaceutical composition disclosed herein into a dermal layer of the skin. Also provided is a use of a product disclosed herein or a pharmaceutical composition disclosed herein for treating the skin of a subject, wherein the product or the pharmaceutical composition is topically applied to the skin or delivered into a dermal layer of the skin. In some embodiments, the delivering into the dermal layer is by injection. In some embodiments, the injection into the dermal layer is by injection using a syringe-fitted with a needle or a microneedling device. In some embodiments, the delivery to the skin is before, during, or after a skin procedure. In some embodiments, the skin procedure is a laser procedure, a chemical procedure, or a mechanical procedure. In some embodiments, the mechanical procedure is a dermabrasion procedure or a microneedling procedure. In some embodiments, the treating comprises reducing the signs of scars, trauma, aging, or sun damage. In some embodiments, the treating comprises healing a wound. In some embodiments, the wound is caused by surgery, abrasion, laceration, or chemicals. In some embodiments, the wound is a diabetic ulcer or a pressure ulcer. In some embodiments, Also provided herein is a method of treating an eye of a subject comprising delivering a product disclosed herein or a pharmaceutical composition disclosed herein to the eye by topical administration. Also provided is a use of a product disclosed herein or a pharmaceutical composition disclosed herein for treating the eye of a subject, wherein the product or the pharmaceutical composition is delivered by topical administration to the eye. In some embodiments, the product or the pharmaceutical composition is delivered to the cornea, the conjunctiva layer, or the sclera of the eye. In some embodiments, the delivery to the eye is before, during, or after an eye procedure. In some embodiments, the eye procedure is a laser procedure or a surgical procedure. In some embodiments, the laser procedure is an ablation procedure. In some embodiments, the surgical procedure is a keratotomy. In some embodiments, the treating comprises treating a wound. In some embodiments, the wound is caused by surgery, abrasion, laceration, or chemicals. In some embodiments, the wound is a corneal ulcer. In some embodiments, the treating comprises reducing the signs or symptoms of dry eye.

Also provided is a method of treating a joint of a subject comprising delivering a product disclosed herein or a pharmaceutical composition disclosed herein to the joint by injection or direct application. Also provided is a use of a product disclosed herein or a pharmaceutical composition disclosed herein for treating a joint of a subject, wherein the product or the pharmaceutical composition is delivered by injection or direct application to the joint. In some embodiments, the joint is a knee, a hip, an elbow, an ankle, a wrist, or a shoulder.

Also provided is a method of treating the spine of a subject comprising delivering a product disclosed herein or a pharmaceutical composition disclosed herein to the spine by injection or direct application. Also provided is a use of a product disclosed herein or a pharmaceutical composition disclosed herein for treating the spine of a subject, wherein the product or the pharmaceutical composition is delivered by injection or direct application to the spine. In some embodiments, the delivery to the joint or spine is before, during, or after a surgical procedure. In some embodiments, the surgical procedure is an arthroscopic procedure. In some embodiments, the treating comprises lubricating or cushioning the joint or the spine. In some embodiments, the treating comprises reducing inflammation in the joint or the spine.

In any of the uses or methods of treating disclosed herein, the subject may be a human.

DETAILED DESCRIPTION OF CERTAIN EMBODIMENTS

Figure 1:
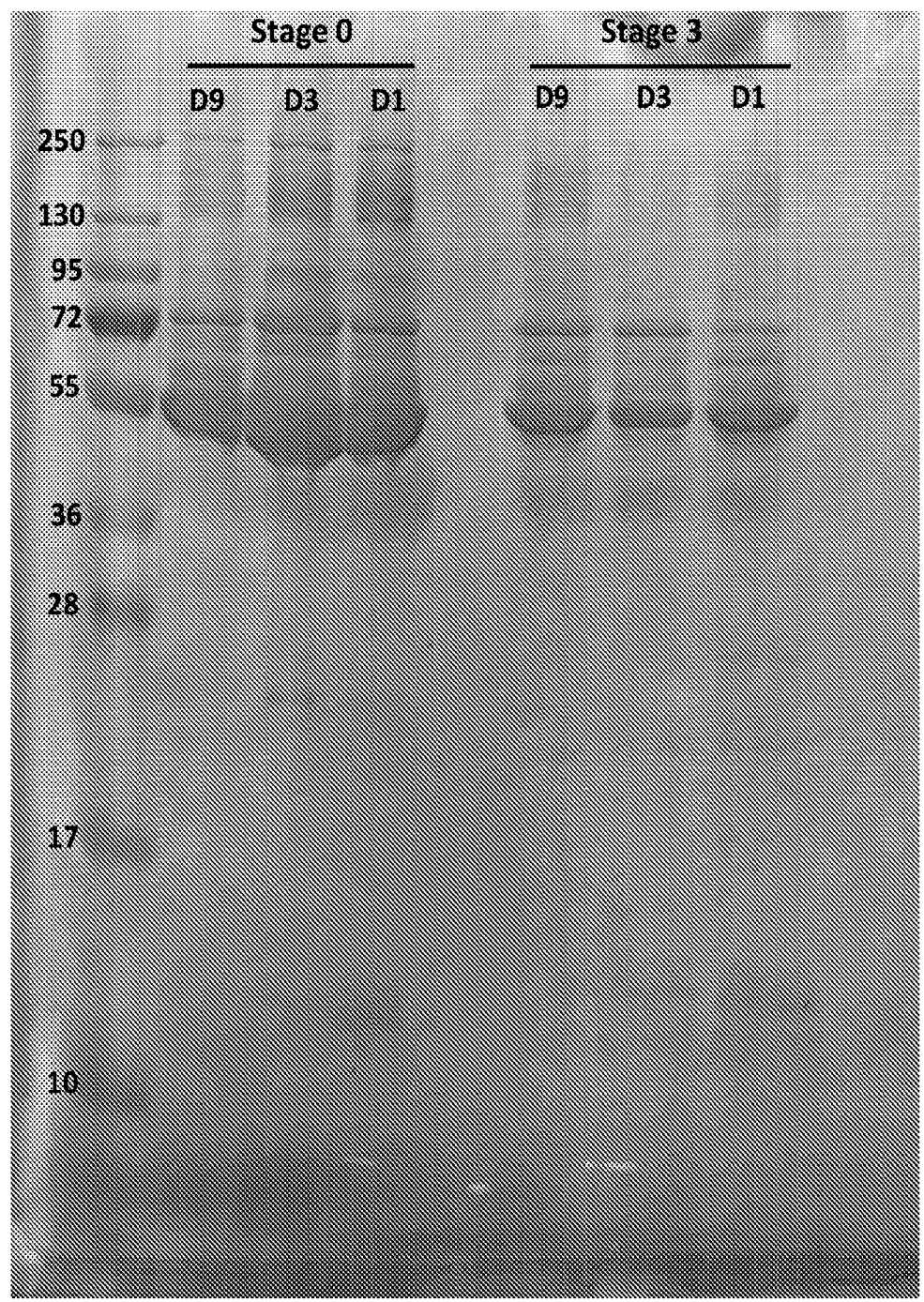
FIG. 1 provides SDS-PAGE analysis of Stage 0 filtrate and Stage 3 lyophilized protein fractions for Donors 1, 3, and 9.

As used herein, the term "about" refers to a numeric value, including, for example, whole numbers, fractions, and percentages, whether or not explicitly indicated. The term "about" generally refers to a range of numerical values (e.g., +/−5-10% of the recited range) that one of ordinary skill in the art would consider equivalent to the recited value (e.g., having the same function or result). When terms such as at least and about precede a list of numerical values or ranges, the terms modify all of the values or ranges provided in the list. In some instances, the term about may include numerical values that are rounded to the nearest significant figure.

As used herein, "a" or "an" means "at least one" or "one or more" unless specified otherwise. As used herein, the term "or" means "and/or" unless specified otherwise. In the context of a multiple dependent claim, the use of "or" when referring back to other claims refers to those claims in the alternative only.

A. Exemplary Components of Amniotic Fluid

Amniotic fluid contains many components, including stem cells, adherent cells, blood cells, proteins, peptides, organic molecules, and electrolytes.

1. Exemplary Amniotic Cells

As used herein "amniotic cells" or a "population of amniotic cells" refers to a group of cells obtained from amniotic fluid. The group of cells may comprise various cell types, including stem cells, adherent cells, blood cells, epithelial cells, fibroblast cells, muscle cells, or nerve cells.

Blood cells may include red blood cells (erythrocytes) and white blood cells (leukocytes such as neutrophils, eosinophils, or lymphocytes).

As used herein "stem cells," "amniotic stem cells," "undifferentiated stem cells," and "stem cells derived from amniotic fluid" are used interchangeably throughout to refer to cells that are capable of differentiating into or producing, in the presence of a differentiation-inducing factor, at least one different cell lineage, such as osteogenic, adipogenic, chondrogenic, myogenic, neurogenic, epithelial, or other cell lineages. Stem cells derived from amniotic fluid can include mesenchymal stem cells, hematopoietic progenitor cells, embryonic stem cells, embryonic-like stem cells, or other stem cells, all of which are considered "undifferentiated" for purposes of this disclosure. In one embodiment, stem cells derived from amniotic fluid may be mesenchymal stem cells that give rise to one or more lineage cells, such as osteoblasts, adipocytes, or chondrocytes. See Roubelakis, M. G., et al., (2007), *Stem Cells Dev.* 16(6): 931-952. In another embodiment, stem cells derived from amniotic fluid may be Epithelial-like (E-like) stem cells, Fibroblast-like (F-like) stem cells, or mixed stem cells. See Pipino, C. L., et al., (2014), *Stem Cells Der.* 24(12):1415-1428.

As used herein, "adherent cells" or "cells that adhere" are used interchangeably throughout to refer to cells that attach to a surface. The surface may be a culture dish or a filter. Blood cells (leukocytes or erythrocytes) are not adherent.

As used herein "cell culture" and "culture" are used interchangeably throughout to refer to a process of growing cells under a controlled condition outside of their natural environment. As used herein "uncultured amniotic cells" or "uncultured cells derived from amniotic fluid," are used interchangeably throughout to refer to cells derived from amniotic fluid that have not been subjected to cell culture.

2. Exemplary Proteins Derived from Amniotic Fluid

Proteins, some of which are likely to contribute to fetal development including, but not limited to, cytokines and growth factors, are released into the amniotic fluid from various tissues of the fetus, the amniotic membrane, and placental tissues. Several hundred proteins have been identified in amniotic fluid for the purpose of improving prenatal diagnosis of disease or conditions.

In some embodiments, the product derived from amniotic fluid may comprise one or more of epidermal growth factor (EGF), transforming growth factor alpha (TGFa), transforming growth factor beta (TGFβ), insulin-like growth factor I (IGF-I), insulin-like growth factor II (IGF-II), erythropoietin (EPO), granulocyte colony-stimulating factor (G-CSF), a tissue inhibitor of metallopeptidase (TIMP), lactoferrin (LF), alpha defensin 1 (HNP1), alpha defensing 2 (HPN2), alpha defensing 3 (HPN3), or interleukin 1A receptor (IL-1Ra).

Other proteins identified in amniotic fluid include those listed in Table 1, as previously described in Michaels, J. E. et al., (2007), *J Proteome Res.* 6(4): 1277-1285 and US Application 20090055099). In some embodiments, the product derived from amniotic fluid comprises at least 1, 2, 3, 4, 5, 6, 7, 8, 9, 10, 11, or 12 first proteins chosen from epidermal growth factor (EGF), transforming growth factor alpha (TGFa), transforming growth factor beta (TGFβ), insulin-like growth factor I (IGF-I), insulin-like growth factor II (IGF-II), erythropoietin (EPO), granulocyte colony-stimulating factor (G-CSF), a tissue inhibitor of metallopeptidase (TIMP), lactoferrin (LF), alpha defensin 1 (HNP1), alpha defensing 2 (HPN2), alpha defensing 3 (HPN3), or interleukin 1A receptor (IL-1Ra), and optionally further comprises at least 1, 2, 3, 4, 5, 6, 7, 8, 9, 10, 11, or 12 additional proteins listed in Table 1 which are different from the first proteins. In some embodiments, the product derived from amniotic fluid comprises at least 10%, 20%, 30%, 40%, 50%, 60%, 70%, 80%, 90%, or 95% of the proteins listed above or in Table 1.

TABLE 1

| UniProtKB Accession No. | Description |
| --- | --- |
| Q2XP30 | Mutant beta-globin |
| P05997 | Collagen alpha-2(V) chain |
| Q14036 | Alpha-2 type I collagen |
| P62328 | Thymosin beta-4 |
| Q07654 | Trefoil factor 3 |
| P35321 | Cornifin-A |
| P11684 | Uteroglobin |
| P04080 | Cystatin B |
| P02652 | Apolipoprotein A-II |
| P10599 | Thioredoxin |
| P05109 | Protein S100-A8 |
| P06702 | Protein S100-A9 |
| P31949 | Protein S100-A11 |
| Q02325 | Plasminogen-related protein B |
| P01040 | Cystatin-A |
| P62805 | Histone H4 |
| P0C0S8 | Histone H2A type 1 |
| P33778 | Histone H2B type 1-B |
| P01595 | Ig kappa chain V-I region Bi |
| P01598 | Ig kappa chain V-I region EU |
| P01603 | Ig kappa chain V-I region Ka |
| P01605 | Ig kappa chain V-I region Lay |
| P04206 | Ig kappa chain V-III region GOL |
| P18135 | Ig kappa chain V-III region HAH |
| P01621 | Ig kappa chain V-III region NG9 |
| P01624 | Ig kappa chain V-III region POM |
| P01622 | Ig kappa chain V-III region Ti |
| P04434 | Ig kappa chain V-III region VH |
| P01625 | Ig kappa chain V-IV region Len |
| P01834 | Ig kappa chain C region |
| P0CG05 | Ig lambda-2 chain C regions |
| P01766 | Ig heavy chain V-III region BRO |
| P01767 | Ig heavy chain V-III region BUT |
| P01215 | Glycoprotein hormones alpha chain |
| P61769 | Beta-2-microglobulin |
| P13987 | CD59 glycoprotein |
| P03973 | Antileukoproteinase |
| P01034 | Cystatin C |
| P09228 | Cystatin-SA |
| P02766 | Transthyretin |
| P69905 | Hemoglobin subunit alpha |
| P68871 | Hemoglobin subunit beta |
| P02042 | Hemoglobin subunit delta |
| P69891 | Hemoglobin subunit gamma-1 |
| P69892 | Hemoglobin subunit gamma-2 |
| P61626 | Lysozyme C |
| P61916 | Epididymal secretory protein E1 |
| P16949 | Stathmin |
| P07998 | Ribonuclease pancreatic |
| P62979 | Ubiquitin-40S ribosomal protein S27a |
| P62987 | Ubiquitin-60S ribosomal protein L40 |
| P07737 | Profilin-1 |
| P60660 | Myosin light polypeptide 6 |
| Q9UBC9 | Small proline-rich protein 3 |
| P23528 | Cofilin-1 |
| P31025 | Lipocalin-A |
| P49913 | Cathelicidin antimicrobial peptide |
| P01344 | Insulin-like growth factor II |
| P09466 | Glycodelin |
| P17900 | Ganglioside GM2 activator |
| P41222 | Prostaglandin-H2 D-isomerase |
| P05976 | Myosin light chain 1/3, skeletal muscle isoform |
| P05090 | Apolipoprotein D |
| P05452 | Tetranectin |
| P80188 | Neutrophil gelatinase-associated lipocalin |
| Q9Y5Z4 | Heme-binding protein 2 |
| P15814 | Immunoglobulin lambda-like polypeptide 1 |
| P02753 | Retinol-binding protein 4 |
| P01033 | Metalloproteinase inhibitor 1 |
| P02763 | Alpha-1-acid glycoprotein 1 |
| P19652 | Alpha-1-acid glycoprotein 2 |
| Q92520 | Protein FAM3C |
| P0DML3 | Chorionic somatomammotropin hormone 2 |
| P0DML2 | Chorionic somatomammotropin hormone 1 |
| Q14406 | Chorionic somatomammotropin hormone-like 1 |
| P13727 | Bone marrow proteoglycan |
| P22352 | Glutathione peroxidase 3 |
| P08294 | Extracellular superoxide dismutase [Cu—Zn] |
| P01236 | Prolactin |
| P20160 | Azurocidin |
| P00746 | Complement factor D |
| P04156 | Major prion protein |
| O95633 | Follistatin-related, protein 3 |
| P62258 | 14-3-3 protein epsilon |
| P61981 | 14-3-3 protein gamma |
| P31947 | 14-3-3 protein sigma |
| P63104 | 14-3-3 protein zeta/delta |
| P08833 | Insulin-like growth factor binding-protein 1 |
| P18065 | Insulin-like growth factor-binding protein 2 |
| P17936 | Insulin-like growth factor-binding protein 3 |
| P22692 | Insulin-like growth factor-binding protein 4 |
| P24593 | Insulin-like growth factor-binding protein 5 |
| Q16270 | Insulin-like growth factor-binding protein 7 |
| P18669 | Phosphoglycerate mutase 1 |
| P00918 | Carbonic anhydrase 2 |
| P02647 | Apolipoprotein A-I |
| P60174 | Triosephosphate isomerase |
| P25311 | Zinc-alpha-2-glycoprotein |
| P09486 | SPARC |
| Q12841 | Follistatin-related protein 1 |
| P10451 | Osteopontin |
| Q10588 | ADP-ribosyl cyclase/cyclic ADP-ribose hydrolase 2 |
| P01876 | Ig alpha-1 chain C region |
| P01877 | Ig alpha-2 chain C region |
| P01857 | Ig gamma-1 chain C region |
| P01859 | Ig gamma-2 chain C region |
| P01860 | Ig gamma-3 chain C region |
| P01861 | Ig gamma-4 chain C region |
| Q03591 | Complement factor H-related protein 1 |
| P29279 | Connective tissue growth factor |
| P02749 | Beta-2-glycoprotein 1 |
| P51884 | Lumican |
| P40121 | Macrophage-capping protein |
| P04083 | Annexin A1 |
| P07355 | Annexin A2 |
| P09525 | Annexin A4 |
| P02750 | Leucine-rich alpha-2-glycoprotein |
| P02760 | Protein AMBP |

TABLE 1-continued

| UniProtKB Accession No. | Description |
|---|---|
| P48745 | Protein NOV homolog |
| P02765 | Alpha-2-HS-glycoprotein |
| P08571 | Monocyte differentiation antigen CD14 |
| P80370 | Protein delta homolog 1 |
| P08174 | Complement decay-accelerating factor |
| P60709 | Actin, cytoplasmic 1 |
| P53485 | Actin, cytoplasmic 2 |
| P68133 | Actin, alpha skeletal muscle |
| Q9UGM5 | Fetuin-B |
| P07988 | Pulmonary surfactant-associated protein B |
| P36222 | Chitinase-3-like protein 1 |
| P30740 | Leukocyte elastase inhibitor |
| Q96MH4 | CDNA FLJ32377 fis, clone SKMUS1000014, highly similar to Polyubiquitin 9 |
| P04278 | Sex hormone-binding globulin |
| P07093 | Glia-derived nexin |
| P29508 | Serpin B3 |
| P48594 | Serpin B4 |
| O75830 | Serpin I2 |
| P00558 | Phosphoglycerate kinase 1 |
| P08185 | Corticosteroid-binding globulin |
| P06727 | Apolipoprotein A-IV |
| P36955 | Pigment epithelium-derived factor |
| P05543 | Thyroxine-binding globulin |
| P01009 | Alpha-1-antitrypsin |
| P11464 | Pregnancy-specific beta-1-glycoprotein 1 |
| P01011 | Alpha-1-antichymotrypsin |
| Q15113 | Procollagen C-endopeptidase enhancer 1 |
| Q96IY4 | Carboxypeptidase B2 |
| P31146 | Coronin-1A |
| P02679 | Fibrinogen gamma chain |
| P08709 | Coagulation factor VII |
| P02790 | Hemopexin |
| Q8TDL5 | BPI fold-containing family B member 1 |
| P10909 | Clusterin |
| P01008 | Antithrombin-III |
| P02774 | Vitamin D-binding protein |
| P01019 | Angiotensinogen |
| P04217 | Alpha-1B-glycoprotein |
| P04004 | Vitronectin |
| P08697 | Alpha-2-antiplasmin |
| Q12805 | EGF-containing fibulin-like extracellular matrix protein 1 |
| P55058 | Phospholipid transfer protein |
| P05155 | Plasma protease C1 inhibitor |
| P02675 | Fibrinogen beta chain |
| P05546 | Heparin cofactor 2 |
| P05362 | Intercellular adhesion molecule 1 |
| P07602 | Prosaposin |
| O43278 | Kunitz-type protease inhibitor 1 |
| Q9UBI9 | Headcase protein homolog |
| P04196 | Histidine-rich glycoprotein |
| Q16610 | Extracellular matrix protein 1 |
| P43251 | Biotinidase |
| P19440 | Gamma-glutamyltranspeptidase 1 |
| P02748 | Complement component C9 |
| Q92496 | Complement factor H-related protein 4 |
| P05156 | Complement factor I |
| Q8TAY0 | Insulin-like growth factor binding protein, acid labile subunit |
| P00748 | Coagulation factor XII |
| P26038 | Moesin |
| P29401 | Transketolase |
| P07476 | Involucrin |
| P02771 | Alpha-fetoprotein |
| Q13421 | Mesothelin precursor |
| P43652 | Afamin |
| P02768 | Serum albumin |
| P00734 | Prothrombin |
| P13796 | Plastin-2 |
| Q9UJ14 | Gamma-glutamyltransferase 7 |
| P03952 | Plasma kallikrein |
| Q6EMK4 | Vasorin |
| P01042 | Kininogen-1 |
| Q15582 | Transforming growth factor-beta-induced protein IG-H3 |
| O00187 | Mannan-binding lectin serine protease 2 |
| P02787 | Serotransferrin |
| P23142 | Fibulin-1 |

TABLE 1-continued

| UniProtKB Accession No. | Description |
|---|---|
| P02788 | Lactotransferrin |
| P55290 | Cadherin-13 |
| P14780 | Matrix metalloproteinase-9 |
| Q5KU26 | Collectin-12 |
| P16070 | CD44 antigen |
| P49747 | Cartilage oligomeric matrix protein |
| P06681 | Complement C2 |
| P01833 | Polymeric-immunoglobulin receptor |
| P05164 | Myeloperoxidase |
| Q16819 | Meprin A subunit alpha |
| P00751 | Complement factor B |
| P06396 | Gelsolin |
| P00747 | Plasminogen |
| P10643 | Complement component C7 |
| P02671 | Fibrinogen alpha chain |
| Q14118 | Dystroglycan |
| P12830 | Cadherin-1 |
| P35609 | Alpha-actinin-2 |
| P19823 | Inter-alpha-trypsin inhibitor, heavy chain H2 |
| P07333 | Macrophage colony-stimulating factor 1 receptor |
| P02452 | Collagen alpha-1(I) chain |
| P02461 | Collagen alpha-1(III) chain |
| P20908 | Collagen alpha-1(V) chain precursor |
| P12109 | Collagen alpha-1(VI) chain |
| P08123 | Collagen alpha-2(I) chain |
| P12111 | Collagen alpha-3 (VI) chain |
| P15144 | Aminopeptidase N |
| P00450 | Ceruloplasmin |
| P07996 | Thrombospondin-1 |
| P14543 | Nidogen-1 |
| Q14112 | Nidogen-2 |
| P08603 | Complement factor H |
| P01023 | Alpha-2-macroglobulin |
| Q14766 | Latent-transforming growth factor beta-binding protein 1 |
| P01024 | Complement C3 |
| P0C0L5 | Complement C4-B |
| P0C0L4 | Complement C4-A |
| Q14767 | Latent-transforming growth factor beta-binding protein 2 |
| Q9UGM3 | Glycoprotein 340 |
| P02751 | Fibronectin |
| P35555 | Fibrillin-1 |
| P22105 | Tenascin-X |
| P98160 | Basement membrane-specific heparan sulfate proteoglycan core protein |
| Q9HC84 | Mucin-5B |

In some embodiments, the product derived from amniotic fluid may comprise one or more of brain-derived neurotrophic factor, basic fibroblast growth factor, chemokine (C-C motif) ligand 28, chemokine (C-X-C motif) ligand 16, endocrine gland-derived vascular endothelial growth factor, eotaxin, eotaxin-2, growth differentiation factor 15, chemokine (C-C motif) ligand 14, hepatocyte growth factor, I-309, insulin-like growth factor binding protein, insulin-like growth factor binding protein-1, insulin-like growth factor binding protein-2, insulin-like growth factor binding protein-3, insulin-like growth factor binding protein-4, insulin-like growth factor binding protein-6, interleukin-6, interleukin-8, monocyte chemotactic protein-1, macrophage colony-stimulating factor, macrophage inhibitory factor, osteoprotegerin, osteopontin, pulmonary and activation-regulated chemokine, PDGF-AA, or PF4.

3. Exemplary Other Components of Amniotic Fluid

In addition to cells and proteins, amniotic fluid also contains biochemical materials, such as bilirubin, bile acid, electrolytes (such as sodium, potassium, chloride, calcium, phosphate, magnesium, bicarbonate, etc.), glucose, cholesterol, triglyceride, urea, creatinine, uric acid, amino acids, and peptides consisting of two amino acids. (see Tong, X. L., et al., (2009), *J Chin. Med. Assoc.* 72(7): 368-373). As used herein, "electrolytes" refers to minerals in amniotic fluid that carry an electric charge, including, but not limited to, sodium, potassium, chloride, calcium, phosphate, magnesium, or bicarbonate. In some embodiments, the products derived from amniotic fluid are substantially free of one or more of urea, electrolytes, amino acids, or peptides consisting of 2 amino acids, bilirubin, bile acid, glucose, cholesterol, triglyceride, urea, creatinine, or uric acid. As used herein, "substantially free" refers to a significantly reduced amount of an agent referenced.

B. Exemplary Embodiments for Processing of Amniotic Fluid

1. Exemplary Embodiments for Collecting Amniotic Fluid

Amniotic fluid may be collected from a human or other mammal, including but not limited to, a primate, artiodactyl, perissodactyl, cow, bison, horse, pig, goat, or the like. Amniotic fluid may be recovered from a human during an amniocentesis or during a C-section. Potential donor mothers may be screened for risk factors to determine whether the amniotic fluid is safe and suitable for donation or processing. In one embodiment, a donor mother is tested for one or more viruses or bacteria using serological tests, which can include without limitation antibody, nucleic acid, or culture testing. The viral or bacterial screen may include screening for the human immunodeficiency virus type 1 or type 2 (HIV-1 and HIV-2), the hepatitis B virus (HBV), the hepatitis C virus (HCV), human T-lymphotropic virus type I or type II (HTLV-I and HTLV-II), CMV, or *Treponema pallidum* (a bacterium that causes syphilis). The amniotic fluid of a donor mother may be considered acceptable based on review of her health information or any screening test results.

Amniotic fluid may be recovered during an elective C-section procedure performed in a sterile operating room environment. Collection may be achieved by drawing amniotic fluid from the mother into a collection container using a needle or tubing via low-level suction or gravity. See US 2014/0336600. At the time of collection, cultures of the collected amniotic fluid may be taken to determine the presence of bacteria, such as *Clostridium* or *Streptococcus*.

Collected amniotic fluid may be packaged in a sterile container, labeled, and shipped on wet ice to a processing laboratory for further processing and evaluation. If the donor mother's health information, screening tests, and cultures are satisfactory (i.e., indicate no risk or acceptable level of risk to human handling or use), the amniotic fluid may be processed for human medical applications.

After opening the shipment at the processing laboratory, personnel may verify that the sterile container is still sealed and in coolant, and that the donor number on the accompanying paperwork matches the number on the sterile container. Processing of donor amniotic fluid for human medical applications may be conducted in a controlled, aseptic environment, such as in a hood or clean room.

2. Exemplary Embodiments for Preparing Amniotic Cells

One advantage of certain embodiments of the present invention is the ability to aseptically process a large volume of amniotic fluid, such as that obtained during a C-section. For example, a 1 L or greater sample of amniotic fluid may be processed using the methods described herein. A sample of amniotic fluid may be processed according to the methods of the invention having a volume, including, but not limited to a volume of about 1 mL, about 10 mL, about 15 mL, about 20 mL, about 25 mL, about 50 mL, about 75 mL, about 100 mL, about 150 mL, about 200 mL, about 250 mL, about 500 mL, about 600 mL, about 700 mL, about 750 mL, about 800 mL, or about 900 mL, about 1 L, about 1.1 L, about 1.2 L, about 1.3 L, about 1.4 L, about 1.5 L, about 1.6 L, about 1.7 L, about 2 L, about 2.2 L, about 2.5 L, about 2.7 L, about 3 L, about 3.2 L about 3.5 L, about 3.7 L, about 4 L, about 4.2 L, about 4.5 L, about 4.7 L, about 5 L, about 5.2 L about 5.5 L, about 5.7 L, about 6 L, about 6.2 L, about 6.5 L, about 6.7 L, or about 7 L, or less than any value listed above, greater than any value listed above, at least any value listed above, or a range of values bounded by any two of the values listed above.

Debris (including clumps) may be removed from a sample of amniotic fluid filtration via mechanical pressure, gravity, or suction, or by low-speed centrifugation. In one embodiment, the amniotic fluid may be pre-filtered by gravity through a polymer filter (e.g., polypropylene, nylon, or polyester, etc.) or metal filter. As used throughout, "filter" may include mesh, sieve, or netting. In another embodiment, the filter has a pore size or diameter size appropriate to retain debris without substantially affecting the flow of the amniotic fluid through the filter. In a further embodiment, the pore size of the filter is 75 µm, 100 µm, or 150 µm. In another embodiment, debris may be removed by pre-filtering the amniotic fluid through cheesecloth or other suitable filtration medium, as will be appreciated by those skilled in the art.

In some embodiments, a sample of amniotic fluid is passed through a cell-separation filter. A sample of amniotic fluid that is passed through a cell-separation filter may be unfiltered amniotic fluid or pre-filtered amniotic fluid. A sample of amniotic fluid may contain debris. A sample of amniotic fluid may be a resuspended pellet from centrifuged amniotic fluid. A sample of amniotic fluid may be uncentrifuged.

As used herein, "cell-separation filter" refers to a filter capable of retaining amniotic cells. In some embodiments, the cells may be retained by the cell-separation filter by size-exclusion or by adherence. In some embodiments, blood cells may pass through the cell-separation filter. In some embodiments, the cell-separation filter is a polymer filter. The polymer filter may be a polypropylene filter, a nylon filter, or a polyester filter. The cell-separation filter may have a size cut off of about 3 µm, about 4 µm, about 5 µm, about 6 µm, about 7 µm, about 8 µm, about 9 µm, about 10 µm, about 11 µm, about 12 µm, about 13 µm, about 14 µm, about 15 µm, about 16 µm, about 17 µm, about 18 µm, about 19 µm, about 20 µm, about 21 µm, about 22 µm, about 23 µm, about 24 µm, about 25 µm, about 26 µm, about 27 µm, about 28 µm, about 29 pun, about 30 µm, about 31 µm, about 32 µm, or about 33 µm, or less than any value listed above, greater than any value listed above, at least any value listed above, or a range of values bounded by any two of the values listed above, such as about 3 to about 33 µm, about 5 to about 25 µm, about 10 to about 20 µm, about 3 to about 20 µm, about 3 to about 10 µm, about 10 to about 33 µm, or about 20 to about 33 µm.

In some embodiments, the cell-separation filter is a closed system. As used herein, "closed system" refers to a device or system where the inside of the device or system is not exposed to the atmosphere.

A sample of amniotic fluid may be passed or forced through the cell-separation filter via mechanical pressure, gravity, vacuum, centrifugation, or agitation. A vacuum may be used to control the rate at which the amniotic fluid passes through the cell-separation filter.

The filtrate may be retained for further processing, such as for preparing protein fractions. Amniotic cells retained by the cell-separation filter may be collected by mechanical methods (e.g., flushing or use of a cell scraper, or etc.) or by chemical treatment (e.g., enzymatically removing with trypsin, chymnotrypsin, or papain, etc.). The collected cells may be suspended in a medium. The medium may be suitable for maintaining viability of the amniotic cells, including, but not limited to physiological saline, phosphate buffered saline, DMEM, or MEM, at temperatures lower than about 37° C. (e.g., at a temperature of about 25° C., about 15° C., or about 5° C.).

A suspension of collected amniotic cells may be concentrated in a volume much smaller than the original sample of amniotic fluid. The amniotic cells may be fractionated to enrich for subpopulations of amniotic cells. For example, the suspension of collected amniotic cells may be fractionated by size via filtration, or by size and density via centrifugation to obtain a stem cell-enriched fraction. In some embodiments, a suspension of collected cells may be passed through one filter or a series of filters. For example, a suspension of collected cells may be passed through one filter or a series of filters having a pore size of about 10 µm, about 25 µm, or about 30 µm to retain amniotic cells having a diameter of about 30 µm or more.

A subpopulation of collected amniotic cells may also be obtained by using cell-surface ligand binding methods understood by those skilled in the art, such as those described in U.S. Pat. Nos. 8,021,876 and 8,940,294. For example, antibodies to cell-surface ligands (e.g., c-Kit, E-cadherin, etc.) may be used to select for specific stem cells.

3. Exemplary Embodiments for Preparing Protein Fractions

As a sample of amniotic fluid is passed through a cell-separation filter, the flow-through filtrate containing non-adherent cells, proteins, and other biomaterials may be collected for further processing. In one embodiment, the filtrate is fractionated into one or more protein fractions. As used herein "protein fraction" refers to a sample comprising two or more proteins derived from amniotic fluid. The sample may include, but is not limited to, proteins on a filter, in a pellet, in a suspension, in a liquid or frozen state, in lyophilized form, in powder form, in a pharmaceutical composition, or any other form discussed herein or known to those of ordinary skill in the art.

The protein-containing filtrate may be fractionated by any number of methods understood by those of ordinary skill in the art, including, but not limited to filtration, centrifugation, or chromatography methods. For example, the protein-containing filtrate may be fractionated by size via filtration using one filter or a series of filters having a molecular weight cut off or size cut off. A filter may, for example, have a molecular weight cut off of about 100 kDa, about 50 kDa, about 30 kDa, about 10 kDa, about 5 kDa, about 3 kDa, about 2 kDa, or about 1 kDa, or less than any value listed above, greater than any value listed above, at least any value listed above, or a range of values bounded by any two of the values listed above, such as about 100 kDa to 1 kDa, about 100 kDa to about 10 kDa, about 100 kDa to about 50 kDa, about 50 kDa to about 10 kDa, about 30 kDa to about 10 kDa, about 10 kDa to about 1 kDa, about 10 kDa to about 5 kDa, or about 5 kDa to about 1 kDa.

Fractionating a protein-containing filtrate may reduce the total content or concentration of one or more biomolecules. In some embodiments, fractionating a protein-containing filtrate according to the methods of the present invention reduces the total content or concentration of one or more of electrolytes, urea, amino acids, peptides of 2 amino acids, or other biomolecules. A protein fraction may have a reduced total content or concentration of one or more of electrolytes, urea, amino acids, peptides of 2 amino acids, or other biomolecules compared to the protein-containing filtrate from which it was fractionated.

Fractionating a protein-containing filtrate may also increase the concentration of one or more protein fractions having a molecular weight range. A protein fraction may have a higher concentration of proteins having a molecular weight range compared to the protein-containing filtrate from which it was fractionated.

Prior to or after fractionating a protein-containing filtrate, residual cells and debris that flow through the cell-separation filter may be removed by any number of methods, including, but not limited to separation by size or density via filtration or centrifugation. In one embodiment, the residual cells or debris are removed by filtration using a filter having a pore size of 50 µm, or other filter or a series of filters having a pore size appropriate to retain cells or debris. The residual cells may also be lysed prior to removal of cell debris using any of the above-described methods.

4. Exemplary Embodiments for Combining Products Derived from Amniotic Fluid

Any amniotic cell or protein fraction product derived from amniotic fluid described herein may be combined prior to or after cryopreservation, dehydration, partial dehydration, lyophilization, preparation as a powder, reconstitution, or other manipulation. For example, the one or more amniotic cell product may be combined with one or more protein fraction product. In one embodiment, two different protein fractions derived from amniotic fluid are combined prior to lyophilization and preparation as a powder. In another embodiment, the combined protein fraction powder is further combined with lyophilized amniotic cell powder before or after reconstitution in an appropriate medium, such as water or saline. Any number of additional combinations of amniotic cell or protein fraction products derived from amniotic fluid described herein could be prepared by one of ordinary skill in the art.

5. Exemplary Embodiments for Preserving Products Derived from Amniotic Fluid

Products comprising amniotic cells or protein fractions may be preserved by any number of methods understood by those of ordinary skill in the art, including, but not limited to, cryopreservation, dehydration, refrigerated, or freezing. A product comprising amniotic cells may be preserved at any processing step. For example, uncultured amniotic cells may be preserved on a cell-separation filter, following collection from a cell-separation filter, in suspension, or after fractionation. Some of the amniotic cells in the preserved product may be viable or maintain the potential to differentiate. For example, a preserved product may include a subpopulation of viable stem cells.

A product comprising a protein fraction may be preserved at any processing step. For example, a protein fraction may be preserved on a filter, following collection from a filter, or after fractionation.

A product comprising uncultured amniotic cells or a protein fraction may be cryopreserved by freezing at, e.g., liquid nitrogen or dry ice temperature, or a temperature of about −200° C. to about −40° C., −200° C. to about −70° C., about −200° C. to about −190° C., or −86° C. to about −78° C. and storing at liquid nitrogen temperatures for up to about 5 years. For example, the cells may be exposed to 5% dimethylsulfoxide (DMSO) and 5% serum in DMEM and frozen slowly or rapidly.

A product comprising uncultured amniotic cells or a protein fraction may be stored at refrigeration temperature for a limited time. For example, a product may be stored at a temperature of about 1° C. to about 12° C. or about 1° C.

to about 5° C. for a time of about 6 hours, about 12 hours, about 18 hours, about 24 hours, about 30 hours, about 36 hours, about 42 hours, about 48 hours, about 54 hours, about 60 hours, about 66 hours, about 72 hours, about 78 hours, about 84 hours, about 90 hours, or less than any time listed above, longer than any time listed above, at least any time listed above, or a range of times bounded by any two of the times listed above.

A product comprising uncultured amniotic cells or a protein fraction may be dehydrated or partially dehydrated in an oven, using chemicals, or by any number of methods known in the art. For example, a product may be dehydrated or partially dehydrated using a dehydration fluid that decreases the water content of the product. A dehydration fluid may be a fluid comprising an alcohol, an organic solvent, a hydrophilic polymer (e.g., polyoxyethylene, a polysaccharide (such as a cellulose derivative or dextrose), etc.) or a salt.

A product comprising uncultured amniotic cells or a protein fraction may also be dehydrated by lyophilization. See, e.g., U.S. Pat. No. 4,001,944 for a discussion of freeze-drying techniques. In some embodiments, a product may be frozen then lyophilized. For example, a product may be quickly frozen using a 100% ethanol/dry ice bath before lyophilizing or frozen less rapidly, e.g., in a freezer, before lyophilizing. In some embodiments, a product may be stored for a period of time at a freezing temperature before lyophilization, such as for about 5 minutes, about 15 minutes, about 30 minutes, about 1 hour, about 2 hours, about 3 hours, about 6 hours, about 12 hours, about 18 hours, about 24 hours, about 30 hours, about 36 hours, about 42 hours, about 48 hours, about 54 hours, about 60 hours, about 66 hours, about 72 hours, about 78 hours, about 84 hours, or about 90 hours, less than any value listed above, greater than any value listed above, at least any value listed above, or a range of values bounded by any two of the values listed above, such as about 5 to about 15 minutes, about 15 to about 30 minutes, about 30 minutes to about 1 hour, about 1 to about 2 hours, about 2 to about 3 hours, about 3 to about 6 hours, about 6 to about 12 hours, about 18 to about 24 hours, about 24 to about 36 hours, about 36 to about 48 hours, about 48 to about 72 hours, or about 72 to about 90 hours.

In another embodiment, partially dehydrated or dehydrated products may be stored for an extended period at a below freezing, freezing, refrigeration, or room temperature. For example, a partially dehydrated and dehydrated product may be stored at a temperature of about −85° C. to about 25° C. (i.e., about −121° F. to about 77° F.) for weeks to years depending on the storage temperature.

Viability of preserved, uncultured amniotic cells may be tested by plating and culturing the cells. Differentiation potential of preserved, uncultured amniotic cells may be tested by plating and culturing the cells in a differentiation-inducing medium. Differentiation-inducing agents such as hydrocortisone, Ca2+, keratinocyte growth factor (KGF), TGF-P, retinoic acid, insulin, prolactin, sodium butyrate, TPA, NMF, DMF, collagen, heparin SO4, androgen, estrogen, and combinations thereof may be used in the medium to induce differentiation into one or more cell lineages. See *Culture of Epithelial Cells*, R. Ian Freshney ed., Wiley-Liss 1992); Kim, J. Y., et al., (2007), *Cell Prolif,* 40(1):75-90.

In another embodiment preserved products may be powderized. As used herein, "powderizing" refers to milling, mincing, grinding, pulverizing, or any other method known in the art to produce a powder. Thus, in some embodiments, a powderized product is milled, minced, ground, or pulverized. For example, a cryopreserved, frozen, partially dehydrated, or dehydrated product may be powderized by using a cryogenic impact grinder (e.g., the 6770, 6870, 6970D, or 6970EFM Spex Freezer/Mill® (Metuchen, N.J.)).

6. Exemplary Sterilization of Products Derived from Amniotic Fluid

Any product derived from amniotic fluid as described herein may be sterilized before, during, or after processing, including after final packaging. Sterilization may be performed using one or more of any of a number of techniques, including, but not limited to exposure to gamma radiation, E-beam radiation, ethylene oxide with a stabilizing gas (such as carbon dioxide or hydrochlorofluorocarbons (HCFC), peracetic acid, hydrogen peroxide gas plasma, or ozone.

C. Exemplary Embodiments for Characterizing Products Derived from Amniotic Fluid The total cell count of a product comprising uncultured amniotic cells prepared according to the methods described herein may range from less than 100 cells to greater than a billion cells. The total cell count of a product may be calculated using a hemocytometer. For example, a product may have a total cell count of about $1\times10^2$, about $2\times10^2$, about $3\times10^2$, about $4\times10^2$, about $5\times10^2$, about $6\times10^2$, about $7\times10^2$, about $8\times10^2$, about $9\times10^2$, about $1\times10^3$, about $2\times10^3$, about $3\times10^3$, about $4\times10^3$, about $5\times10^3$, about $6\times10^3$, about $7\times10^3$, about $8\times10^3$, about $9\times10^3$, about $1\times10^4$ cells, about $2\times10^4$ cells, about $3\times10^4$ cells, about $4\times10^4$ cells, about $5\times10^4$ cells, about $6\times10^4$ cells, about $7\times10^4$ cells, about $8\times10^4$ cells, about $9\times10^4$ cells, about $1\times10^5$ cells, about $2\times10^5$ cells, about $3\times10^5$ cells, about $4\times10^5$ cells, about $5\times10^5$ cells, about $6\times10^5$ cells, about $7\times10^5$ cells, about $8\times10^5$ cells, about $9\times10^5$ cells, about $1\times10^6$ cells, about $2\times10^6$ cells, about $3\times10^6$ cells, about $4\times10^6$ cells, about $5\times10^6$ cells, about $6\times10^6$ cells, about $7\times10^6$ cells, about $8\times10^6$ cells, about $9\times10^6$ cells, about $1\times10^7$ cells, about $2\times10^7$ cells, about $3\times10^7$ cells, about $4\times10^7$ cells, about $5\times10^7$ cells, about $6\times10^7$ cells, about $7\times10^7$ cells, about $8\times10^7$ cells, about $9\times10^7$ cells, about $1\times10^8$ cells, about $2\times10^8$ cells, about $3\times10^8$ cells, about $4\times10^8$ cells, about $5\times10^8$ cells, about $6\times10^8$ cells, about $7\times10^8$ cells, about $8\times10^8$ cells, about $9\times10^8$ cells, or about $1\times10^9$ cells, or less than any value listed above, greater than any value listed above, at least any value listed above, or a range of values bounded by any two of the values listed above, such as about $1\times10^2$ to about $1\times10^3$, about $1\times10^3$ to about $1\times10^4$, about $1\times10^4$ to about $1\times10^5$, about $1\times10^5$ to about $1\times10^6$, about $1\times10^6$ to about $1\times10^7$, about $1\times10^7$ to about $1\times10^8$, about $1\times10^8$ to about $1\times10^9$, about $1\times10^7$ to about $1\times10^9$, about $1\times10^5$ to about $1\times10^8$, about $1\times10^6$ to about $1\times10^8$, about $1\times10^4$ to about $1\times10^7$, or about $1\times10^3$ to about $1\times10^7$.

A product comprising uncultured amniotic cells prepared according to the methods described herein may comprise cells expressing one, two, three, or more markers. The marker may be a stem cell marker, a hematopoietic progenitor cell marker, a mesenchymal stem cell marker, an embryonic stem cell marker. For example, a product may comprise cells expressing c-kit or E-cadherin. Expression of the one or more markers may be determined by any one of a number of methods understood by one of ordinary skill in the art, including but not limited to, an enzyme-linked immunosorbent assay (ELISA) or Fluorescence Activated Cell Sorting (FACS) analysis. For example, a product comprising c-kit positive or E-cadherin positive cells may generate a positive signal when tested by ELISA or FACS.

A product comprising uncultured amniotic cells or a protein fraction may have a decreased water or moisture content. A product may have a residual moisture content of about 1%, about 2%, about 3%, about 4%, about 5%, about 6%, about 7%, about 8%, about 9%, about 10%, about 11%, about 12%, about 13%, about 14%, or about 15%, or less than any percentage listed above, greater than any percentage listed above, at least any percentage listed above, or a range of percentages bounded by any two of the percentages listed above, such as about 1% to about 2%, about 2% to about 3%, about 3% to about 4%, about 4% to about 5%, about 5% to about 6%⁰, about 6% to about 7%, about 7% to about 8%, about 8% to about 9%, about 9% to about 10%, about 10% to about 11%, about 11% to about 12%, about 12% to about 13%, about 13% to about 14%, about 14% to about 15%, about 1% to about 5%, about 5% to about 10%, about 10% to about 15%, about 2% to about 4%, about 4% to about 6%, about 6% to about 8%, about 8% to about 10%, about 10% to about 12%, about 12% to about 14%, about 1% to about 15%, or about 1% to about 10%.

Total protein content of a product prepared according to the methods described herein may range from less than about 1 microgram to greater than about 100 milligrams. A product may have a total protein content of about 1 µg, about 5 µg, about 10 µg, about 20 µg, about 25 µg, about 30 µg, about 40 µg, about 50 µg, about 60 µg, about 70 µg, about 75 µg, about 80 µg, about 90 µg, about 100 µg, about 125 µg, about 150 µg, about 175 µg, about 200 µg, about 225 µg, about 250 µg, about 275 µg, about 300 µg, about 325 µg, about 350 µg, about 375 µg, about 400 µg, about 425 µg, about 450 µg, about 475 µg, about 500 µg, about 525 µg, about 550 µg, about 575 µg, about 600 µg, about 625 µg, about 650 µg, about 675 µg, about 700 µg, about 750 µg, about 800 µg, about 850 µg, about 900 µg, about 950 µg, about 1 mg, about 5 mg, about 10 mg, about 20 mg, about 25 mg, about 30 mg, about 40 mg, about 50 mg, about 60 mg, about 70 mg, about 75 mg, about 80 mg, about 90 mg, or about 100 mg, or less than any value listed above, greater than any value listed above, at least any value listed above, or a range of values bounded by any two of the values listed above, such as about 1 µg to about 10 µg, about 10 µg to about 100 µg, about 100 µg to about 1 mg, about 1 mg to about 10 mg, about 10 mg to about 100 mg, about 1 µg to about 25 µg about 25 µg to about 50 µg, about 100 µg to about 250 µg, about 250 µg to about 500 µg, about 500 to about 750 µg, about 500 µg to about 1 mg, about 1 mg to about 100 mg, about 1 µg to about 100 µg, or about 100 µg to about 10 mg.

Total protein content per mass of a product prepared according to the methods described herein may range from less than about 1 to greater than 300 micrograms per milligram of product. A product may have a total protein content per mass of product of about 1 µg/mg, about 5 µg/mg, about 10 µg/mg, about 15 µg/mg, about 20 µg/mg, about 25 µg/mg, about 30 µg/mg, about 35 µg/mg, about 40 µg/mg, about 45 µg/mg, about 50 µg/mg, about 55 µg/mg, about 60 µg/mg, about 65 µg/mg, about 70 µg/mg, about 75 µg/mg, about 80 µg/mg, about 85 µg/mg, about 90 µg/mg, about 95 µg/mg, about 100 µg/mg, about 110 µg/mg, about 120 µg/mg, about 130 µg/mg, about 140 µg/mg, about 150 µg/mg, about 160 µg/mg, about 170 µg/mg, about 180 µg/mg, about 190 µg/mg, about 200 µg/mg, about 210 µg/mg, about 220 µg/mg, about 230 µg/mg, about 240 µg/mg, about 250 µg/mg, about 260 µg/mg, about 270 µg/mg, about 280 µg/mg, about 290 µg/mg, or about 300 µg/mg, or less than any value listed above, greater than any value listed above, at least any value listed above, or a range of values bounded by any two of the values listed above, such as about 1 µg/mg to about 10 µg/mg, about 10 µg/mg to about 25 µg/mg, about 25 µg/mg to about 50 µg/mg, about 50 µg/mg to about 75 µg/mg, about 75 µg/mg to about 100 µg/mg, about 100 µg/mg to about 150 µg/mg, about 150 µg/mg to about 200 µg/mg, about 200 µg/mg to about 250 µg/mg, about 250 µg/mg to about 300 µg/mg, about 1 µg/mg to about 100 µg/mg, about 100 µg/mg to about 300 µg/mg, about 50 µg/mg to about 200 µg/mg, or about 200 µg/mg to about 300 µg/mg.

Total protein content per volume of a product prepared according to the methods described herein may range from less than about 1 micrograms per milliliter to greater than 15 milligrams per milliliter of product. A product may have a total protein content per volume of product of about 1 µg/mL, about 5 µg/mL, about 10 µg/mL, about 15 µg/mL, about 25 µg/mL, about 30 µg/mL, about 40 µg/mL, about 50 µg/mL, about 60 µg/mL, about 70 µg/mL, about 75 µg/mL, about 80 µg/mL, about 90 µg/mL, about 100 µg/mL, about 125 µg/mL, about 150 µg/mL, about 175 µg/mL, about 200 µg/mL, about 225 µg/mL, about 250 µg/mL, about 275 µg/mL, about 300 µg/mL, about 350 µg/mL, about 400 µg/mL, about 450 µg/mL, about 500 µg/mL, about 600 µg/mL, about 700 µg/mL, about 800 µg/mL, about 900 µg/mL, about 1 mg/mL, about 2 mg/mL, about 3 mg/mL, about 4 mg/mL, about 5 mg/mL, about 6 mg/mL, about 7 mg/mL, about 8 mg/mL, about 9 mg/mL, about 10 mg/mL, about 11 mg/mL, about 12 mg/mL, about 13 mg/mL, about 14 mg/mL, or about 15 mg/mL, or less than any value listed above, greater than any value listed above, at least any value listed above, or a range of values bounded by any two of the values listed above, such as about 1 µg/mL to about 10 µg/mL, about 10 µg/mL to about 25 µg/mL, about 25 µg/mL to about 50 µg/mL, about 50 µg/mL to about 100 µg/mL, about 100 µg/mL to about 250 µg/mL, about 250 µg/mL to about 500 µg/mL, about 500 µg/mL to about 700 µg/mL, about 700 µg/mL to about 1 mg/mL, about 1 mg/mL to about 5 mg/mL, about 5 mg/mL to about 15 mg/mL, about 1 µg/mL to about 15 mg/mL, about 1 µg/mL to about 100 µg/mL, about 1 µg/mL to about 1 mg/mL, about 10 µg/mL to about 1 mg/mL, or about 500 µg/mL.

A product prepared according to the methods described herein may comprise proteins having a molecular weight ranging from less than 1 kDa to greater than 600 kDa under non-reducing conditions. A product may comprise proteins having a molecular weight of about 1 kDa, about 2 kDa, about 5 kDa, about 10 kDa, about 20 kDa, about 30 kDa, about 40 kDa, about 50 kDa, about 60 kDa, about 70 kDa, about 80 kDa, about 90 kDa, about 100 kDa, about 120 kDa, about 140 kDa, about 160 kDa, about 180 kDa, about 200 kDa, about 220 kDa, about 240 kDa, about 260 kDa, about 280 kDa, about 300 kDa, about 350 kDa, about 400 kDa, about 450 kDa, about 500 kDa, about 550 kDa, or about 600 kDa, or less than any value listed above, greater than any value listed above, at least any value listed above, or a range of values bounded by any two of the values listed above, such as about 1 kDa to about 5 kDa, about 5 kDa to about 10 kDa, about 10 kDa to about 50 kDa, about 50 kDa to about 100 kDa, about 100 kDa to about 150 kDa, about 150 kDa to about 200 kDa, about 200 kDa to about 250 kDa, about 250 kDa to about 300 kDa, about 300 kDa to about 400 kDa, about 400 kDa to about 500 kDa, about 500 kDa to about 600 kDa, about 1 kDa to about 50 kDa, about 50 kDa to about 250 kDa, about 250 kDa to about 500 kDa, or about 100 kDa to about 600 kDa.

Hemoglobin is a major component of erythrocytes (or red blood cells) and is responsible for the cells' characteristic red color. The hemoglobin content of a product prepared according to the methods described herein may range from less than about 3 milligrams to 0.01 micrograms. The hemoglobin content is the total hemoglobin mass in a product. A procedure for determining hemoglobin content is provided in Example 20 below.

In some embodiments, the hemoglobin content may be undetectable for a product prepared according to the methods described herein. For example, the hemoglobin content may be undetectable in an ELISA assay. The ELISA assay can have one or more the features of the ELISA assay described in Example 20. In other embodiments, a product may have a hemoglobin content of about 3 mg, about 2 mg, about 1 mg, about 900 µg, about 800 µg, about 700 µg, about 600 µg, about 500 µg, about 400 µg, about 300 µg, about 200 µg, about 100 µg, about 50 µg, about 40 µg, about 30 µg, about 20 µg, about 10 µg, about 9 µg, about 8 µg, about 7 µg, about 6 µg, about 5 µg, about 4 µg, about 3 µg, about 2 µg, about 1 µg, about 0.9 µg, about 0.8 µg, about 0.7 µg, about 0.6 µg, about 0.5 µg, about 0.4 µg, about 0.3 µg, about 0.2 µg, about 0.1 µg, about 0.09 µg, about 0.08 µg, about 0.07 µg, about 0.06 µg, about 0.05 µg, about 0.04 µg, about 0.03 µg, about 0.02 µg, or about 0.01 µg, or less than any value listed above, greater than any value listed above, at least any value listed above, or a range of values bounded by any two of the values listed above, such as about 3 mg to about 1 mg, about 1 mg to about 500 µg, about 500 µg to 100 µg, about 100 µg to about 50 µg, about 50 µg to about 10 µg, about 10 µg to about 5 µg, about 5 µg to about 1 µg, about 1 µg to about 0.5 µg, about 0.5 µg to about 0.1 µg, about 0.1 µg to about 0.05 µg, about 0.05 µg to about 0.01 µg, about 50 µg to about 0.1 µg, about 50 µg to about 5 µg, about 5 µg to about 0.5 µg, about 0.5 µg to about 0.05 µg, about 1 µg to about 0.01 µg, about 0.1 µg to about 0.01 µg, about 3 mg to about 0.01 µg, about 3 mg to about 300 µg, about 300 µg to about 30 µg, or about 3 mg to about 30 µg.

The hemoglobin content per dry mass of a product prepared according to the methods described herein may range from less than about 10 micrograms per milligram to 0.01 micrograms per milligram. In some embodiments, a product may have hemoglobin content per dry mass of the product of about 10 µg/mg, about 9 µg/mg, about 8 µg/mg, about 7 µg/mg, about 6 µg/mg, about 5 µg/mg, about 4 µg/mg, about 3 µg/mg, about 2 µg/mg, about 1 µg/mg, about 0.9 µg/mg, about 0.8 µg/mg, about 0.7 µg/mg, about 0.6 µg/mg, about 0.5 µg/mg, about 0.4 µg/mg, about 0.3 µg/mg, about 0.2 µg/mg, about 0.1 µg/mg, about 0.09 µg/mg, about 0.08 µg/mg, about 0.07 µg/mg, about 0.06 µg/mg, about 0.05 µg/mg, about 0.04 µg/mg, about 0.03 µg/mg, about 0.02 µg/mg, or about 0.01 g/mg, or less than any value listed above, greater than any value listed above, at least any value listed above, or a range of values bounded by any two of the values listed above, such as about 10 µg/mg to about 5 µg/mg, about 5 µg/mg to about 1 µg/mg, about 1 µg/mg to about 0.5 µg/mg, about 0.5 µg/mg to about 0.1 µg/mg, about 0.1 µg/mg to about 0.05 µg/mg, about 0.05 µg/mg to about 0.01 µg/mg, about 10 µg/mg to about 1 µg/mg, about 1 µg/mg to about 0.1 µg/mg, about 0.1 µg/mg to about 0.1 µg/mg to about 0.01 µg/mg, about 10 µg/mg to about 0.01 µg/mg, about 1 µg/mg to about 0.01 µg/mg, or about 5 µg/mg to about 0.05 µg/mg.

The hemoglobin content per volume of a product prepared according to the methods described herein may range from less than about 10 micrograms per milliliter to 0.01 micrograms per milliliter. In some embodiments, a product may have hemoglobin content per volume of the product of about 10 µg/mL, about 9 µg/mL, about 8 µg/mL, about 7 µg/mL, about 6 µg/mL, about 5 µg/mL, about 4 µg/mL, about 3 µg/mL, about 2 µg/mL, about 1 µg/mL, about 0.9 µg/mL, about 0.8 µg/mL, about 0.7 µg/mL, about 0.6 µg/mL, about 0.5 µg/mL, about 0.4 µg/mL, about 0.3 µg/mL, about 0.2 µg/mL, about 0.1 µg/mL, about 0.09 µg/mL, about 0.08 µg/mL, about 0.07 µg/mL, about 0.06 µg/mL, about 0.05 µg/mL, about 0.04 µg/mL, about 0.03 µg/mL, about 0.02 µg/mL, or about 0.01 µg/mL, or less than any value listed above, greater than any value listed above, at least any value listed above, or a range of values bounded by any two of the values listed above, such as about 10 µg/mL to about 5 µg/mL, about 5 µg/mL to about 1 µg/mL, about 1 µg/mL to about 0.5 µg/mL, about 0.5 µg/mL, to about 0.1 µg/mL, about 0.1 µg/mL to about 0.05 µg/mL, about 0.05 µg/mL to about 0.01 µg/mL, about 10 µg/mL to about 1 µg/mL, about 1 µg/mL to about 0.1 µg/mL, about 0.1 µg/mL, about 0.1 µg/mL to about 0.01 µg/mL, about 10 µg/mL to about 0.01 µg/mL, about 1 µg/mL to about 0.01 µg/mL, or about 5 µg/mL to about 0.05 µg/mL.

The urea content of a product prepared according to the methods described herein may range from less than about 300 micrograms to 0.01 micrograms. The urea content is the total urea mass in a product. A procedure for determining urea content is provided in Example 20 below.

In some embodiments, the urea content may be undetectable for a product prepared according to the methods described herein. For example, the urea content may be undetectable in colorimetric assay. The colorimetric assay can have one or more the features of the assay described in Example 20. In other embodiments, a product may have a urea content of about 300 µg, about 250 µg, about 200 µg, about 150 µg, about 100 µg, about 90 µg, about 80 µg, about 70 µg, about 60 µg, about 50 µg, about 40 µg, about 30 µg, about 20 µg, about 10 µg, about 9 µg, about 8 µg, about 7 µg, about 6 µg, about 5 µg, about 4 µg, about 3 µg, about 2 µg, about 1 µg, about 0.9 µg, about 0.8 µg, about 0.7 µg, about 0.6 µg, about 0.5 µg, about 0.4 µg, about 0.3 µg, about 0.2 µg, about 0.1 µg, about 0.09 µg, about 0.08 µg, about 0.07 µg, about 0.06 µg, about 0.05 µg, about 0.04 µg, about 0.03 µg, about 0.02 µg, or about 0.01 µg, or less than any value listed above, greater than any value listed above, at least any value listed above, or a range of values bounded by any two of the values listed above, such as about 300 µg to about 200 µg, about 200 µg to about 100 µg, about 100 µg to about 50 µg, about 50 µg to about 20 µg, about 20 µg to about 10 µg, about 10 g to about 5 µg, about 5 µg to about 1 µg, about 1 µg to about 0.5 µg, about 0.5 µg to about 0.1 µg, about 0.1 µg to about 0.05 µg, about 0.05 µg to about 0.01 µg, about 300 µg to about 150 µg, about 150 µg to about 50 µg, about 50 µg to about 10 µg, about 10 µg to about 1 µg, about 1 µg to about 0.1 µg, about 0.1 to about 0.01 µg, about 300 µg to about 10 µg, about 10 µg to about 0.1 µg, about 50 µg to about 0.5 µg, about 0.5 µg to about 0.05 µg, or about 300 µg to about 0.01 µg.

The urea content per dry mass of a product prepared according to the methods described herein may range from less than about 100 micrograms per milligram to 0.01 micrograms per milligram. In some embodiments, a product may have urea content per dry mass of the product of about 100 µg/mg, about 90 µg/mg, about 80 µg/mg, about 70 µg/mg, about 60 µg/mg, about 50 µg/mg, about 40 µg/mg, about 30 µg/mg, about 20 µg/mg, about 10 µg/mg, about 9 µg/mg, about 8 µg/mg, about 7 µg/mg, about 6 µg/mg, about 5 µg/mg, about 4 µg/mg, about 3 µg/mg, about 2 µg/mg, about 1 µg/mg, about 0.9 g/mg, about 0.8 µg/mg, about 0.7 µg/mg, about 0.6 µg/mg, about 0.5 µg/mg, about 0.4 µg/mg, about 0.3 µg/mg, about 0.2 µg/mg, about 0.1 µg/mg, about 0.09 µg/mg, about 0.08 µg/mg, about 0.07 µg/mg, about 0.06 µg/mg, about 0.05 µg/mg, about 0.04 µg/mg, about 0.03 µg/mg, about 0.02 µg/mg, or about 0.01 µg/mg, or less than any value listed above, greater than any value listed above, at least any value listed above, or a range of values bounded by any two of the values listed above, such as about 100 µg/mg to about 50 µg/mg, about 50 µg/mg to about 10 µg/mg, about 10 µg/mg to about 5 g/mg, about 5 µg/mg to about 1 µg/mg, about 1 µg/mg to about 0.5 µg/mg, about 0.5 µg/mg to about 0.1 µg/mg, about 0.1 µg/mg to about 0.05 µg/mg, about 0.05 µg/mg to about 0.01 µg/mg, about 100 µg/mg to about 10 µg/mg, about 10 µg/mg to about 1 µg/mg, about 1 µg/mg to about 0.1 µg/mg, about 0.1 µg/mg to about 0.01 µg/mg, about 100 µg/mg to about 1 µg/mg, about 1 to about 0.01 µg/mg, about 50 µg/mg to about 1 µg/mg, about 50 µg/mg to about 0.05 µg/mg, about 5 µg/mg to about 0.5 µg/mg, about 100 µg/mg to about 0.01 µg/mg.

The urea content per volume of a product prepared according to the methods described herein may range from less than about 100 micrograms per milliliter to 0.01 micrograms per milliliter. In some embodiments, a product may have urea content per volume of the product of about 100 µg/mL, about 90 µg/mL, about 80 µg/mL, about 70 µg/mL, about 60 µg/mL, about 50 µg/mL, about 40 µg/mL, about 30 µg/mL, about 20 µg/mL, about 10 µg/mL, about 9 µg/mL, about 8 µg/mL, about 7 µg/mL, about 6 µg/mL, about 5 µg/mL, about 4 µg/mL, about 3 µg/mL, about 2 µg/mL, about 1 µg/mL, about 0.9 µg/mL, about 0.8 µg/mL, about 0.7 µmL, about 0.6 µg/mL, about 0.5 µg/mL, about 0.4 µg/mL, about 0.3 µg/mL, about 0.2 µg/mL, about 0.1 µg/mL, about 0.09 µg/mL, about 0.08 µg/mL, about 0.07 µg/mL, about 0.06 µg/mL, about 0.05 µg/mL, about 0.04 µg/mL, about 0.03 µg/mL, about 0.02 µg/mL, or about 0.01 µg/mL, or less than any value listed above, greater than any value listed above, at least any value listed above, or a range of values bounded by any two of the values listed above, such as 100 µg/mL to about 50 µg/mL, about 50 µg/mL to about 10 µg/mL, about 10 µg/mL to about 5 µg/mL, about 5 µg/mL to about 1 µg/mL, about 1 µg/mL to about 0.5 µg/mL, about 0.5 µg/mL to about 0.1 µg/mL, about 0.1 µg/mL to about 0.05 µg/mL, about 0.05 µg/ml, to about 0.01 µg/mL, about 100 µg/mL, to about 10 µg/mL, about 10 µg/mL to about 1 µg/mL, about 1 µg/mL to about 0.1 µg/mL, about 0.1 µg/mL to about 0.01 µg/mL, about 100 µg/mL to about 1 µg/mL, about 1 to about 0.01 µg/mL, about 50 µg/mL to about 1 µg/mL, about 50 µg/mL to about 0.05 µg/mL, about 5 µg/mL to about 0.5 µg/mL, about 100 µg/mL to about 0.01 g/mL.

In some embodiments, the component(s) sought to be removed from a product prepared according to the methods described herein is one or more of blood cells, red blood cells, white blood cells, urea, electrolytes, amino acids, peptides consisting of 2 amino acids, bilirubin, bile acid, glucose, cholesterol, triglyceride, creatinine, or uric acid. In some embodiments, a product is substantially free of one or more of blood cells, red blood cells, white blood cells, urea, electrolytes, amino acids, peptides consisting of 2 amino acids, bilirubin, bile acid, glucose, cholesterol, triglyceride, creatinine, or uric acid. As used herein, "substantially free" refers to a significantly reduced amount of an agent referenced. In some embodiments, the reduction in amount is greater than about 50%. In some embodiments, the reduction in amount is greater than about 60%, about 70%, about 80%, about 90%, about 91%, about 92%, about 93%, about 94%, about 95%, about 96%, about 97%, about 98%, or about 99%.

In some embodiments, substantially free of red blood cells means that the hemoglobin content is undetectable or less than about 3 mg hemoglobin per product. In some embodiments, substantially free of red blood cells means that the hemoglobin content is less than about 2 mg, about 1 mg, about 900 µg, about 800 µg, about 700 µg, about 600 µg, about 500 µg, about 400 µg, about 300 µg, about 200 µg, about 100 µg, about 50 µg, about 40 µg, about 30 µg, about 20 µg, about 10 µg, about 9 µg, about 8 µg, about 7 µg, about 6 µg, about 5 µg, about 4 µg, about 3 µg, about 2 µg, about 1 µg, about 0.9 µg, about 0.8 µg, about 0.7 µg, about 0.6 µg, about 0.5 µg, about 0.4 µg, about 0.3 µg, about 0.2 µg, about 0.1 µg, about 0.09 µg, about 0.08 µg, about 0.07 µg, about 0.06 µg, about 0.05 µg, about 0.04 µg, about 0.03 µg, about 0.02 µg, or about 0.01 µg.

In other embodiments, substantially free of red blood cells means that the hemoglobin content per mass of the product ("µg/mg") is less than about 10 µg/mg, about 9 µg/mg, about 8 µg/mg, about 7 µg/mg, about 6 µg/mg, about 5 µg/mg, about 4 µg/mg, about 3 µg/mg, about 2 µg/mg, about 1 µg/mg, about 0.9 µg/mg, about 0.8 µg/mg, about 0.7 µg/mg, about 0.6 µg/mg, about 0.5 µg/mg, about 0.4 µg/mg, about 0.3 µg/mg, about 0.2 µg/mg, about 0.1 µg/mg, about 0.09 µg/mg, about 0.08 µg/mg, about 0.07 µg/mg, about 0.06 µg/mg, about 0.05 µg/mg, about 0.04 µg/mg, about 0.03 µg/mg, about 0.02 µg/mg, or about 0.01 µg/mg.

In some embodiments, substantially free of red blood cells means that the hemoglobin content per volume of the product ("µg/mL") is less than about 10 µg/mL, about 9 µg/mL, about 8 µg/mL, about 7 µg/mL, about 6 µg/mL, about 5 µg/mL, about 4 µg/mL, about 3 µg/mL, about 2 µg/mL, about 1 µg/mL, about 0.9 µg/mL, about 0.8 µg/mL, about 0.7 µg/mL, about 0.6 µg/mL, about 0.5 µg/mL, about 0.4 µg/mL, about 0.3 µg/mL, about 0.2 µg/mL, about 0.1 µg/mL, about 0.09 µg/mL, about 0.08 µg/mL, about 0.07 µg/mL, about 0.06 µg/mL, about 0.05 µg/mL, about 0.04 µg/mL, about 0.03 µg/mL, about 0.02 µg/mL, or about 0.01 µg/mL.

In some embodiments, substantially free of urea means that the urea content is undetectable or less than about 300 µg urea per product. In some embodiments, substantially free of urea means that the urea content is less than about 250 µg, about 200 µg, about 150 µg, about 100 µg, about 90 µg, about 80 µg, about 70 µg, about 60 µg, about 50 µg, about 40 µg, about 30 µg, about 20 µg, about 10 µg, about 9 µg, about 8 µg, about 7 µg, about 6 µg, about 5 µg, about 4 µg, about 3 µg, about 2 µg, about 1 µg, about 0.9 µg, about 0.8 µg, about 0.7 µg, about 0.6 µg, about 0.5 µg, about 0.4 µg, about 0.3 µg, about 0.2 µg, about 0.1 µg, about 0.09 µg, about 0.08 µg, about 0.07 µg, about 0.06 µg, about 0.05 µg, about 0.04 µg, about 0.03 µg, about 0.02 µg, or about 0.01 µg.

In other embodiments, substantially free of urea means that the urea content per mass of the product ("µg/mg") is less than about 100 µg/mg, about 90 µg/mg, about 80 µg/mg, about 70 µg/mg, about 60 µg/mg, about 50 µg/mg, about 40 µg/mg, about 30 µg/mg, about 20 µg/mg, about 10 µg/mg, about 9 µg/mg, about 8 µg/mg, about 7 µg/mg, about 6 µg/mg, about 5 µg/mg, about 4 µg/mg, about 3 µg/mg, about 2 µg/mg, about 1 µg/mg, about 0.9 µg/mg, about 0.8 µg/mg, about 0.7 µg/mg, about 0.6 µg/mg, about 0.5 µg/mg, about 0.4 µg/mg, about 0.3 µg/mg, about 0.2 µg/mg, about 0.1 µg/mg, about 0.09 µg/mg, about 0.08 µg/mg, about 0.07 g/mg, about 0.06 µg/mg, about 0.05 µg/mg, about 0.04 µg/mg, about 0.03 µg/mg, about 0.02 µg/mg, or about 0.01 µg/mg.

In some embodiments, substantially free of red blood cells means that the urea content per volume of the product ("µg/mL") is less than about 100 µg/mL, about 90 µg/mL, about 80 µg/mL, about 70 µg/mL, about 60 µg/mL, about 50 µg/mL, about 40 µg/mL, about 30 µg/mL, about 20 µg/mL, about 10 µg/mL, about 9 µg/mL, about 8 µg/mL, about 7

µg/mL, about 6 µg/mL, about 5 µg/mL, about 4 µg/mL, about 3 µg/mL, about 2 µg/mL, about 1 µg/mL, about 0.9 µg/mL, about 0.8 µg/mL, about 0.7 µg/mL, about 0.6 µg/mL, about 0.5 µg/mL, about 0.4 µg/mL, about 0.3 µg/mL, about 0.2 µg/mL, about 0.1 µg/mL, about 0.09 µg/mL, about 0.08 µg/mL, about 0.07 µg/mL, about 0.06 µg/mL, about 0.05 µg/mL, about 0.04 µg/mL, about 0.03 µg/mL, about 0.02 µg/mL, or about 0.01 µg/mL.

The mean particle size of a product prepared according to the methods described herein may range from less than about 1 micron to 300 microns. A procedure for determining mean particle size is provided in Example 21 below. In some embodiments, a product may have a mean particle size of about 1 µm, about 5 µm, about 10 µm, about 15 µm, about 20 µm, about 25 µm, about 30 µm, about 35 µm, about 40 µm, about 45 µm, about 50 µm, about 55 µm, about 60 µm, about 65 µm, about 70 µm, about 75 µm, about 80 µm, about 85 µm, about 90 µm, about 95 µm, about 100 µm, about 110 µm, about 120 µm, about 130 µm, about 140 µm, about 150 µm, about 160 µm, about 170 µm, about 180 µm, about 190 µm, about 200 µm, about 210 µm, about 220 µm, about 230 µm, about 240 µm, about 250 µm, about 260 µm, about 270 µm, about 280 µm, about 290 µm, or about 300 µm, or less than any value listed above, greater than any value listed above, at least any value listed above, or a range of values bounded by any two of the values listed above, such as about 1 µm to about 5 µm, about 5 µm to about 25 µm, about 25 µm to about 50 µm, about 50 µm to about 100 µm, about 100 µm to about 150 µm, about 150 µm to about 300 µm, about 1 µm to about 100 µm, about 1 µm to about 250 µm, about 1 µm to about 10 µm, about 10 µm to about 100 µm, about 100 µm to about 300 µm, about 25 µm to about 100 µm, about 5 µm to about 50 µm, about 50 µm to about 150 µm, about 50 µm to about 300 µm, or about 1 to about 300 µm.

D. Exemplary Therapeutic Applications

1. Exemplary Pharmaceutical Products

Any amniotic cell or protein fraction product of the invention may be used in therapeutic applications directly or as a pharmaceutical composition. In one embodiment, the pharmaceutical composition may comprise one or more pharmaceutically acceptable carriers and any of the products of the invention. The pharmaceutical composition or pharmaceutically acceptable carrier may comprise a cream, lotion, emulsion, gel, liposome, nanoparticle, spray, or ointment.

In one embodiment, the pharmaceutically acceptable carrier comprises water, saline, or artificial tears. In other embodiments, the pharmaceutically acceptable carrier comprises hyaluronic acid. In additional embodiments, the pharmaceutically acceptable carrier comprises a bulking agent. In some embodiments, the pharmaceutically acceptable carrier comprises a polymer. In another embodiment, the pharmaceutically acceptable carrier comprises a protein carrier, including, but not limited to collagen, fibronectin, elastin, or laminin.

In a further embodiment, the pharmaceutically acceptable carrier comprises a polysaccharide. Examples of polysaccharides include, but are not limited to, celluloses or cellulose derivatives, cellulose ethers (e.g., carboxymethylcellulose, carboxyethylcellucose, hydroxypropylcellulose, hydroxyethylcellulose, hydroxypropyl methylcellulose, or methylcellulose, etc.).

Other examples of polysaccharides include glycosaminoglycans (GAGs) or glucosaminoglycans, with suitable viscosity, molecular mass, or other desirable properties.

By glycosaminoglycan is intended any glycan (i.e., polysaccharide) comprising an unbranched polysaccharide chain with a repeating disaccharide unit, one of which is always an amino sugar. These compounds as a class carry a high negative charge, are strongly hydrophilic, and are commonly called mucopolysaccharides. This group of polysaccharides includes heparin, heparan sulfate, chondroitin sulfate, dermatan sulfate, keratin sulfate, and hyaluronic acid. These GAGs are predominantly found on cell surfaces and in the extracellular matrix.

By glucosaminoglycan is also intended any glycan (i.e., polysaccharide) containing predominantly monosaccharide derivatives in which an alcoholic hydroxyl group has been replaced by an amino group or other functional group such as sulfate or phosphate. An example of a glucosaminoglycan is poly-N-acetyl glucosaminoglycan, commonly referred to as chitosan. Exemplary polysaccharides that may be useful in the present invention include dextran, heparan, heparin, hyaluronic acid, alginate, agarose, cellulose, chitin, chitosan, or various sulfated polysaccharides, such as heparan sulfate, chondroitin sulfate, dextran sulfate, dermatan sulfate, or keratin sulfate.

In one embodiment, the pharmaceutical composition comprises a hydrogel comprising any of the products of the invention. Hydrogels can generally absorb a great deal of fluid and, at equilibrium, typically are composed of 60-90% fluid and only 10-30% polymer. In one embodiment, the water content of the hydrogel is about 70-80%. Hydrogels are useful due to the inherent biocompatibility of the cross-linked polymeric network (Hill-West, et al., (1994), *Proc. Natl. Acad. Sci. USA* 91:5967-5971). Hydrogel biocompatibility may be attributed to hydrophilicity and the ability to imbibe large amounts of biological fluids (Brannon-Peppas. *Preparation and Characterization of Cross-linked Hydrophilic Networks in Absorbent Polymer Technology*, Brannon-Peppas and Harland, Eds. 1990, Elsevier: Amsterdam, pp. 45-66; Peppas and Mikos. *Preparation Methods and Structure of Hydrogels in Hydrogels in Medicine and Pharmacy*, Peppas, Ed. 1986, CRC Press: Boca Raton, Fla., pp 1-27). The hydrogels may be prepared by crosslinking hydrophilic biopolymers or synthetic polymers. Examples of the hydrogels formed from physical or chemical crosslinking of hydrophilic biopolymers include, but are not limited to, hyaluronans, chitosans, alginates, collagen, dextran, pectin, carrageenan, polylysine, gelatin or agarose. (see Bennink, W. E. and van Nostrum, C. F., (2002), *Adv. Drug Del. Rev.* 54, 13-36 and Hoffman, A. S., (2002), *Adv. Drug Del. Rev.* 43, 3-12). These materials consist of high-molecular weight backbone chains made of linear or branched polysaccharides or polypeptides. Examples of hydrogels based on chemical or physical crosslinking synthetic polymers include, but are not limited to, (meth)acrylate oligolactide-PEO-oligolactide-(meth)acrylate, poly(ethylene glycol) (PEO), polypropylene glycol) (PPO), PEO-PPOPEO copolymers (Pluronics), poly(phosphazene), poly(methacrylates), poly(N-vinylpyrrolidone), PL(G)A-PEO-PL(G)A copolymers, poly(ethylene imine), etc. (see A. S. Hoffman, 2002 *Adv. Drug Del. Rev,* 43, 3-12). In some embodiments, the hydrogel may be crosslinked using poly(ethylene glycol) diacrylate (PEGDA) in a photochemical reaction.

In one embodiment, the hydrogel comprises at least one biopolymer. In other embodiments, the hydrogel scaffold further comprises at least two biopolymers. In yet other embodiments, the hydrogel further comprises at least one biopolymer and at least one synthetic polymer. In one embodiment, the hydrogel comprises hyaluronic acid, CMC, collagen, or gelatin and is crosslinked using PEGDA in a photochemical reaction.

In another embodiment, the pharmaceutical composition is a lotion, emulsion, or cream comprising any of the products of the invention. Lotions may be fluid emulsions and creams may be soft-solid or thick-liquid emulsions (e.g., an oil-in-water emulsion or a water-in-oil emulsion). In some embodiments, the hydrophobic component of a lotion or cream is derived from an animal (e.g., lanolin, cod liver oil, or ambergris), plant (e.g., safflower oil, castor oil, coconut oil, cottonseed oil, menhaden oil, palm kernel oil, palm oil, peanut oil, soybean oil, rapeseed oil, linseed oil, rice bran oil, pine oil, sesame oil, or sunflower seed oil), or petroleum (e.g., mineral oil, or petroleum jelly).

In further embodiments, the pharmaceutical composition of the invention comprises a gelling agent or thickener and any of the products of the invention. Suitable gelling agents or thickeners include, but are not limited to, collagen, fibrin, hyaluronic acid, celluloses, cellulose derivatives, cellulose ethers (e.g., carboxymethylcellulose, ethylcellulose, hydroxyethylcellulose, hydroxymethylcellulose, hydroxypropylmethylcellulose, hydroxypropylcellulose, methylcellulose, ethymelthylcellulose), guar gum, xanthan gum, locust bean gum, alginates (e.g., alginic acid), silicates, starch, tragacanth, carboxyvinyl polymers, carrageenan, paraffin, petrolatum, acacia (gum arabic), agar, aluminum magnesium silicate, sodium alginate, sodium stearate, bladderwrack, bentonite, carbomer, carrageenan, carbopol, microcrystalline cellulose (MCC), ceratonia, chondrus, dextrose, furcellaran, gelatin, ghatti gum, hectorite, lactose, sucrose, maltodextrin, mannitol, sorbitol, honey, maize starch, wheat starch, rice starch, potato starch, sterculia gum, polyols (e.g., propyleneglycol, polyethylene glycol, hexylene glycol, glycerol, cremophor or the like), ethylhydroxyethyl cellulose, oxypolygelatin, pectin, polygeline, povidone, propylene carbonate, methyl vinyl ether/maleic anhydride copolymer (PYM/MA), poly(methoxyethyl methacrylate), poly(hydroxyethyl methacrylate), poly(methoxyethoxyethyl methacrylate), silicon dioxide, polyvinylpyrrolidone (PVP: povidone), or combinations thereof.

In other embodiments, pharmaceutically acceptable carriers include, but are not limited to, a bulking agent, ethanol, glycerin, hexylene glycol, phosphoric acid, sodium hydroxide, sodium phosphate, polysorbate 80, vegetable oils (such as olive oil), injectable organic esters (e.g., ethyl oleate), fatty oils (e.g., sesame oil), or triglycerides.

2. Exemplary Embodiments for Dermatological Therapy

The amniotic cell or protein fraction products described herein may be delivered to the skin, including the dermal layer of the skin, of a human in need of treatment. The skin to be treated may be, for example, aged skin (e.g., with wrinkling or loss of collagen), sun-damaged skin (e.g., with discoloration), or scarred skin. Further examples of skin that may be treated using the products of the invention include, but are not limited to, wounded skin, such as skin wounded by surgery, abrasion, laceration, burn (e.g., by chemical or heat). In some embodiments, the products of the invention may be applied to the skin or injected into the dermis before, during, or after a skin procedure. For example, the amniotic cell protein fraction products described herein may be delivered to the skin, including into the dermis of the skin, before, during, or after a skin procedure, such as a laser procedure, a chemical procedure, a mechanical procedure, or other procedure that creates dermal injury. In some embodiments the skin procedure is a laser resurfacing procedure, a dermabrasion procedure, a micro-needling procedure, or a chemical peel, which are commonly used in the medical and cosmetic fields to injure the skin and allow the skin to regenerate. Techniques used in performing skin procedures are understood by those of ordinary skill in the art.

In other embodiments, the products of the invention may be applied topically without any accompanying skin procedure. For example, the amniotic cell or protein fraction products described herein may be applied topically to the skin periodically to improve the appearance of damaged skin, including aged skin (e.g., wrinkled skin or loss of collagen).

The products of the invention may also be used for dermal augmentation by injecting any of the products described herein into the dermis of skin of a human in need of augmentation, such as aged skin (e.g., with wrinkling or loss of collagen), sun-damaged skin, or scarred skin (e.g., depressions of the skin). For example, a sterile syringe (e.g., plastic or glass) fitted with a standard needle (e.g., a 25, 28, 30, or 33 gauge hypodermic needle) and containing about 1 mL to about 3 mL of any of the products of the invention may be injected by multiple, manual injections into the dermis of aged, sun-damaged, or scarred skin.

3. Exemplary Embodiments for Ocular Therapy

In some embodiments, the amniotic cell or protein fraction products described herein are delivered to the eye, including the cornea, the conjunctiva layer, or the sclera, of a human in need of treatment. For example, the amniotic cell or protein fraction products described herein may be delivered to the eye before, during, or after an eye procedure, such as a laser procedure or a mechanical procedure, or other procedure that creates ocular injury. In some embodiments, the amniotic cell or protein fraction products are topically applied to the eye using drops. In some embodiments, drops of the products of the invention are applied on the eye after ocular surface surgery (e.g., Ptyrigium excision), on the bare sclera, or on the cornea.

Exemplary injuries or diseases of the eye that the products disclosed herein may be used to treat are as follows. In some embodiments, a product is used for the reconstruction of the ocular surface in patients with limbal stem cells deficiency (Tseng et al., 1998). In some embodiments, a product is used for the treatment of visual system age-related diseases in general. In some embodiments, a product is used for reconstruction of the ocular surface in patient with corneal persistent epithelial defect (Tseng et al., 1998). In some embodiments, a product is used for corneal epithelial healing and to avoid corneal stromal remodeling and haze formation after photorefractive keratectomy (Woo et al., 2001). In some embodiments, a product is used as a substance that can promote and support healing processes following ocular surface damage related to Stevens Johnson Syndrome and OCP (Tsubota et al., 1996). In some embodiments, a product is used for healing support or a therapeutic approach in other eye anterior surface diseases including dry eye, Sjiigren's syndrome, thermal or chemical burns, or as a versatile compound that can treat the causes of total or partial epithelial stem cells deficiency. In some embodiments, a product is used to treat a total epithelial stem cell deficiency; examples include, but are not limited to, chemical and thermal injuries, Stevens Johnson Syndrome, multi-surgery effects in the limbal region, contact lens over-wear and severe microbial infections. In some embodiments, a product is used to treat a partial epithelial stem cell deficiency; examples include, but are not limited to, neurotrophic keratitis, ischemic keratitis, peripheral ulcerative and inflammatory keratitis, limbitis, aniridia, pterigium, pseudopterigium and multiple endocrine deficiency (Tseng et al., 1998; Uchida et al., 2000).

4. Exemplary Embodiments for Joint Therapy and Spine

Osteoarthritis is a common joint disease that effects many patients as they age. Intrarticular injections of hyaluronic acid or stem cells have been described. In some embodiments, the amniotic cell and protein fraction products described herein are delivered to a joint, including a knee, a hip, an elbow, an ankle, a wrist, or a shoulder, or to the spine of a human in need of treatment. For example, the amniotic cell or protein fraction products described herein may be delivered to the joint by injection or by direct application to a joint or to the spine. In some embodiments the products described herein may reduce pain, may promote healing of cartilage surfaces, or may increase lubrication or cushioning.

EXAMPLES

Example 1. Collection of Amniotic Fluid

Amniotic fluid collected from a donor mother during C-section and deemed safe for handling and use, as described herein, is processed and evaluated.

Example 2. Deriving Uncultured Cells from Amniotic Fluid

The following processing steps are conducted in a controlled, aseptic environment, such as in a hood or clean room. A sample of fresh, non-frozen amniotic fluid (e.g., a sample obtained according to Example 1 and/or having a IL volume) is filtered by gravity through a 100 µm polypropylene filter to remove debris and clumps. The filtrate is then filtered through a cell-separation filter (e.g., Bone Marrow MSC Separation Device, Kaneka Corporation, Japan, Purecell™ Select System for Whole Blood MNC Enrichment (Pall Corporation, MI), or other) to collect cells that adhere to the filter. The protein-containing filtrate is collected for further processing. The adherent cells on the cell-separation filter are detached and collected in suspension by reverse-flushing with a fluid capable of releasing the cells from the filter (e.g., 0.025% trypsin in PBS trypsin in PBS). The cell suspension is filtered through one or more filters of appropriate size and composition to retain a subpopulation of amniotic cells. The cells retained on the filter are reverse-flushed to form a cell suspension of uncultured amniotic cells.

Example 3. Cryopreserving Amniotic Cells

The uncultured amniotic cells from Example 2 are cryopreserved and stored in liquid nitrogen. The cryopreserved amniotic cells are thawed, plated, and cultured in culture flasks to determine viability of the cells. Differentiation potential of the cryopreserved amniotic cells is determined by culturing the cells in a differentiation-inducing medium.

Example 4. Dehydrating Amniotic Cells

Samples of the uncultured amniotic cells from Example 2 are dehydrated using a dehydration fluid capable of decreasing the water content of the cells. Samples of the uncultured amniotic cells from Example 2 are also dehydrated by lyophilization. Viability of the dehydrated amniotic cells is determined by pelleting, resuspending, plating and culturing the cells in culture flasks. Differentiation potential of the dehydrated amniotic cells is determined by culturing the cells in a differentiation-inducing medium.

Example 5. Milling Lyophilized Amniotic Cells

The lyophilized amniotic cells from Example 4 are milled to produce a powder.

Example 6. Cryopreserving Dehydrated Amniotic Cells

The dehydrated amniotic cells from Example 4 are cryopreserved and stored in liquid nitrogen. Viability of the cryopreserved, dehydrated cells is determined by thawing, plating, and culturing the cells in culture flasks. Differentiation potential of the cryopreserved, dehydrated amniotic cells is determined by culturing the cells in a differentiation-inducing medium.

Example 7. Milling Cryopreserved, Dehydrated Amniotic Cells

The cryopreserved, dehydrated amniotic cells from Example 6 are milled to produce a powder.

Example 8. Preparing Protein Fractions

The protein-containing filtrate from the adherent cell-separation step of Example 2 is filtered through a 50 µm filter in order to remove residual cells and debris. The filtrate is then filtered through a 100 kD molecular weight cutoff (mwco) filter to collect a first protein fraction comprising proteins having a molecular weight of 100 kD or greater. The filtrate is then filtered through a 10 kD mwco filter to collect a second protein fraction comprising proteins having a molecular weight of between 100 kD and 10 kD.

The 100 kD mwco filter containing the first protein fraction and the 10 kD mwco filter containing the second protein fraction are weighed. Each protein fraction is eluted with an appropriate buffer into a separate lyophilizing container.

Each protein fraction is dehydrated by lyophilization. Each of the lyophilized protein fractions may be milled to produce a powder of concentrated proteins. Each sample of powder is weighed.

Example 9. Combining Protein Fractions

The first and second protein fractions from Example 8 are combined prior to lyophilization.

Example 10. Pharmaceutical Composition of Amniotic Fluid Components

The lyophilized amniotic cell powder from Example 5 and the combined protein fraction powder from Example 9 are separately packaged, sealed, and sterilized, e.g., using gamma or E-beam radiation. When ready for use, the components are reconstituted in a pharmaceutically acceptable carrier (e.g., saline, hyaluronic acid, carboxymethylcellose, or collagen) and combined.

Example 11. Microneedling Procedure

A sterile syringe containing 5 mL of the amniotic fluid components from Example 10 is topically administered to the facial and neck skin of a human patient before a micro-needling procedure using the PRPen™ (Advanced Dermal Sciences, Jupiter, Fla.). The skin is first cleansed and a topical anesthetic (e.g., a compounded topical gel or cream containing 88% Lidocaine and 4% Tetracaine) is applied to the treatment area and allowed to remain on the skin for a minimum of 20 to 30 minutes to ensure patient comfort.

Once anesthesia is achieved, all traces of anesthetic are removed and the skin is thoroughly cleansed with an anti-bacterial wash (e.g., Chlorhexidine).

The amniotic product is topically applied by releasing a drop from a syringe onto a treatment area without touching the skin. A plastic applicator is used to spread the amniotic product over the treatment area. The PRPen™ is used to needle the amniotic product into the dermal layer of the skin using the recommended depth of penetration and vertical upward strokes.

The PRPen™ has twelve 33-gauge solid needles on each tip that can be adjusted for depth of penetration ranging from about 0 to about 2.5 mm by rotating the head of the tool to the desired unit. A needle depth of about 0.25 mm to about 0.5 mm up to about 0.75 mm is recommended for the forehead, temporal, nose, and neck area of the face. A needle depth of about 0.25 mm to about 1.0 mm is recommended for the upper lip area. A needle depth of about 0.5 to about 1.0 mm up to about 2.0 mm is recommended for the cheeks and chin area. A needle depth of about 0.25 mm is recommended for the periorbital skin area.

The procedure of topically applying the amniotic product followed by needling of the product into the dermal layer is repeated until all treatment areas are completed. The procedure is repeated for optionally a second pass using a horizontal stroke pattern, optionally a third pass using a diagonal stroke pattern, and optionally a fourth pass using a diagonal stroke pattern in the mirror direction. Any remaining amniotic product in the syringe is spread topically to the skin using the plastic applicator. The above procedure is repeated every two weeks until the desired results are achieved.

Example 12. Dermal Augmentation Procedure

A sterile syringe fitted with a needle (e.g., a 25, 28, 30, or 33 gauge hypodermic needle) and containing 1 to 3 mL of the amniotic fluid components from Example 10 is injected by multiple, manual injections into the dermis of an area of human skin in need of augmentation, including aged, sun-damaged, or scarred skin. Following injection of product intradermally, the PRPen™ is used to needle the amniotic product into the dermal layer in order to distribute the product intradermally in the skin.

Before the injection procedure, the skin is cleansed and a topical anesthetic (e.g., a compounded topical gel or cream containing 88% Lidocaine and 4% Tetracaine) is applied to the treatment area and allowed to remain on the skin for a minimum of 20 to 30 minutes to ensure patient comfort. Once anesthesia is achieved, all traces of anesthetic are removed and the skin is thoroughly cleansed with an anti-bacterial wash (e.g., Chlorhexidine). The dermal augmentation procedure may be repeated as necessary.

Example 13. Amniotic Cell Pre-Filtration Method

Amniotic fluid collected from ten donor mothers during C-section was evaluated and deemed safe for handling and use as described herein. Each donor fluid was pre-filtered to remove debris and clumps. Depending on the amount and size of the debris and dumps, the donor fluid may be poured through one or a combination of a coarse polypropylene mesh (e.g., 0.025 inches×0.03 inches), a fine polypropylene mesh (e.g., 0.54 inches×0.08 inches), or a nylon sieve (e.g., 100 μm pores). Amniotic fluid from Donors 1 and 3-10 was passed through a nylon sieve. Amniotic fluid from Donor 6 was first passed through a course mesh then through a nylon sieve. The filtrate (referred to as "pre-filtered amniotic fluid") was aliquoted into 50 mL conical tubes and stored at refrigeration temperature until batch filtration runs were performed.

Example 14. Uncultured Amniotic Cell Filtration Method A

Purecell™ Select System for Whole Blood MNC Enrichment (Pall Corporation, MI), which has a filter made of a medical-grade polyester, was used to obtain a population of uncultured cells from batches of pre-filtered amniotic fluid from Donors 1-8. Before each filtration run, a batch of pre-filtered amniotic fluid was removed from refrigeration and brought to room temperature. A small sample was removed to estimate the total number of cells in the batch using a hemocytometer (see Table 2 for results). For batches from Donors 1 and 2, the estimated total cell count listed in Table 2 was determined after pre-filtration and before ali-quoting and refrigeration.

To assemble the system, the clamps on the three segments of tubing between the filtration unit and (1) the sample input bag, (2) the cell harvest bag, and (3) the filtrate bag were closed to block flow through the system. A volume of pre-filtered amniotic fluid was injected into the sample input bag via the sample input port. The system was assembled on a ring stand with the bottom of the sample input bag hanging from the top of the stand. The clamp between the filter unit and the filtrate bag and the clamp between the sample input bag and the filter unit were released. The sample was left to flow under gravity through the filter unit and into the filtrate bag. When the input bag was empty, the clamps between the filter unit and filtrate bag and sample input bag were closed.

Using a 30 mL syringe, 24 mL of a cell collection medium (DMEM, PBS, or 0.025% trypsin in PBS) was slowly pushed through the filtration unit via a harvest fluid port (connected to the filtration unit) to reverse-flush cells off the filter and into the cell harvest bag. For some batches, the reverse-flush procedure was repeated once or twice with fresh media. For some batches, the filter was reverse-flushed after every 25 mL of pre-filtered amniotic fluid was processed through the system. The volume of donor fluid processed and the cell collection method and medium used for each batch are summarized in Table 2.

At the completion of each batch run, the cell harvest bag was detached from the filter unit and a 30 mL syringe used to transfer the cell suspension (also called "retentate") from the cell harvest bag to a 50 mL conical tube. A small sample was removed from the cell suspension to determine the total number of cells recovered from the filter using a hemocytometer. The remainder of the retentate was centrifuged at 1200-1500 RPM for 20 minutes to pellet the cells. The supernatant was discarded and the cell pellet resuspended in 3 mL of PBS. The resuspended cells were divided equally into two vials and lyophilized.

A 60 mL, syringe was used to transfer the filtrate from the filtrate bag into 50 mL conical tubes and stored in the freezer. A small sample was removed from the filtrate to determine the total number of cells that were not retained by the filter. Table 2 summarizes the volume of fluid processed, cell collection parameters, estimated cell count, and percent cells recovered for filtration of pre-filtered amniotic fluid batches from Donors 1-8 using the Purecell™ system.

TABLE 2

| Donor | Pre-filtered AF batch volume processed (mL) | Cell collection method/medium | Estimated Total Cells Before filtration | Filtrate | Retentate | Percent Cells Recovered |
|---|---|---|---|---|---|---|
| 1 | 65 | A | $4.2 \times 10^7$ | NT | $2.7 \times 10^7$ | 63% |
|  | 85 | B | $5.5 \times 10^7$ | NT | $2.4 \times 10^7$ | 44% |
|  | 83 | C | $5.4 \times 10^7$ | NT | $2.5 \times 10^7$ | 46% |
| 2 | 34 | C | $7.8 \times 10^6$ | NT | $1.5 \times 10^6$ | 19% |
| 3 | 50 | D | $1.9 \times 10^7$ | $2.0 \times 10^5$ | $1.1 \times 10^7$ | 56% |
| 4 | 50 | E | $3.5 \times 10^7$ | ND | $1.5 \times 10^7$ | 41% |
| 5 | 50 | F | $9.3 \times 10^6$ | ND | $6.6 \times 10^6$ | 71% |
| 6 | 100 | F | $4.0 \times 10^7$ | $4.0 \times 10^6$ | $1.5 \times 10^7$ | 38% |
| 7 | 50 | F | $2.6 \times 10^7$ | $4.0 \times 10^5$ | $1.5 \times 10^7$ | 56% |
| 8 | 75 | F | $2.2 \times 10^7$ | $1.5 \times 10^5$ | $8.6 \times 10^6$ | 40% |

Cell collection method and medium A: Reverse-flush filter once with DMEM. B: Reverse-flush filter thrice with DMEM. C: Reverse-flush filter thrice with PBS. D: Reverse-flush filter thrice with PBS after at least 25 mL of processed sample. E: Reverse-flush filter twice with PBS. F: Reverse-flush filter with 0.025% trypsin solution in PBS after every 25 mL of processed sample.
NT = not tested;
ND = not detected

Example 15. Uncultured Amniotic Cell Filtration Method B

A Bone Marrow MSC Separation Device (Kaneka Corporation, Japan) was used to obtain a population of uncultured cells from a batch of pre-filtered amniotic fluid from Donor 2. A Luer lock joint was added to the inlet of the Kaneka filter column and a 3-way stopcock was added to the outlet of the filter column. A 60 mL syringe containing 50 mL of PBS was connected to the Luer lock joint on the inlet side of the filter column. The flow channel on the three-way stopcock was opened and the PBS was gently pushed through the filter column. The flow channel of the outlet was closed and the syringe detached from the inlet. The plunger was removed from the empty syringe, 30 mL of pre-filtered amniotic fluid from Donor 2 (estimated to contain $1.9 \times 10^7$ total cells) was added, and the plunger was replaced. The syringe was reconnected to the Luer lock joint at the filter inlet. The filter column was assembled on a ring stand with the syringe clamped to the ring stand and the syringe tip pointing downward. A conical tube was placed beneath the filter outlet and the flow channel of the stopcock opened. The plunger of the syringe was slowly depressed until its contents were emptied.

The syringe was then removed from the Luer lock joint and the column turned upside down with the filter column clamped to the ring stand and the inlet side of the filter column pointing downward. The air filter on the cell harvest bag was disconnected and the bag was connected to the Luer lock joint at the filter inlet. After removing the cap on the side of the three-way stopcock, a 60 mL syringe was connected to the stopcock and used to gently push 50 mL of PBS through the filter column to flush cells from the filter and into the cell harvest bag. The cell harvest bag was detached from the filter column and a 30 mL syringe used to transfer the cell suspension (also called "retentate") from the cell harvest bag to a 50 mL conical tube.

A small sample of retentate was used to estimate the total number of amniotic fluid cells recovered from the filter. A hemocytometer was used to estimate that the retentate contained $2.9 \times 10^6$ cells equating to a 15% recovery rate. The remainder of the retentate was centrifuged at 1200 RPM for 20 minutes to pellet the cells. The supernatant was discarded and the cell pellet resuspended in 3 mL of PBS. The resuspended cells were divided equally into two vials and lyophilized.

Example 16. Uncultured Amniotic Cell Filtration Method C

CellMicroSieves™ (BioDesign Inc., NY) made of a woven matrix of nylon filaments and having pore sizes of 5 and 10 μm were used to obtain a population of uncultured cells from batches of pre-filtered amniotic fluid from Donors 1-5, 7, 9, and 10. A 250 mL capacity filtration chamber (Thermo Scientific™ Nalgene™ Reusable Filter Holder with Receiver, Product No. 09-740-23A) with an input chamber and filtrate chamber was assembled as follows. The sieves were cut to fit the circular membrane support plates (47 mm in diameter). The sieves were placed adjacent to one another on a single membrane support plate and added to the upper chamber in descending order with the 10 μm sieve on top of the 5 μm sieve. A vacuum line was applied to one of the side ports and the other ports were sealed.

Before each filtration run, a batch of pre-filtered amniotic fluid was removed from refrigeration and brought to room temperature. A small sample was removed to estimate the total number of cells in the batch using a hemocytometer. See Table 3 for results. 20 mL (Donors 1-5 and 9) or 25 mL (Donors 7 and 10) of pre-filtered amniotic fluid was applied to the upper chamber. Vacuum (250 mbar) was applied to the chamber during filtration of batches from Donors 3-5, 7, 9, and 10. No vacuum was applied to during filtration of batches from Donors 1 and 2.

After the fluid had been pulled through the chamber, any vacuum was turned off and the device was disassembled. Tweezers were used to remove the sieves. For Donors 1, 3-5, and 9, each sieve was placed in a dish containing 5 mL of PBS and gently agitated. For Donor 2, each sieve was placed in a dish containing 12 mL of PBS and gently agitated. For Donors 7 and 10, each sieve was placed in a dish containing 5 mL of 0.05% trypsin in PBS for 10 minutes. A cell scraper was used to gently remove the cell layer off of each sieve. Each sieve was then transferred to an empty dish and the cell scraper was used to gently remove any remaining cells and liquid. The cell suspensions (also called "retentate") were combined into a 50 mL conical tube.

The filtration chamber was reassembled in the same manner as before using the same 10 μm and 5 μm sieves. The filtration and cell collection steps were repeated until the remainder of the batch of pre-filtered amniotic fluid had been processed. Between each donor fluid processed, the sieves were soaked in warm water with detergent then rinsed and air dried overnight.

A small sample was removed from the combined cell suspension to determine the total number of cells recovered from the sieves using a hemocytometer. The remainder of the retentate was centrifuged at 1200 to 2000 RPM for 20 minutes to pellet the cells. The supernatant was discarded and the cell pellet resuspended in 3 mL (Donors 1-5 and 9) or 10 mL of PBS (Donors 7 and 10). The resuspended cells were lyophilized. The filtrate was transferred into 50 mL conical tubes and stored in the freezer. A small sample of the filtrate was removed to determine the total number of cells that were not retained by the sieves. Table 3 summarizes the volume of fluid processed, estimated cell count, and percent cells recovered for filtration of pre-filtered amniotic fluid batches from Donors 1-5, 7, 9, and 10 using the BioDesign sieves.

TABLE 3

| Donor | Pre-filtered AF batch volume processed (mL) | Estimated Total Cells | | | Percent Cells Recovered |
| --- | --- | --- | --- | --- | --- |
| | | Before filtration | Filtrate | Retentate | |
| 1 | 50 | $2.9 \times 10^7$ | $3.6 \times 10^6$ | $1.3 \times 10^7$ | 45% |
| 2 | 38 | $8.7 \times 10^6$ | $4.3 \times 10^6$ | $1.6 \times 10^6$ | 19% |
| 3 | 50 | $8.0 \times 10^6$ | $1.0 \times 10^6$ | $6.0 \times 10^6$ | 75% |
| 4 | 40 | $2.8 \times 10^7$ | $1.6 \times 10^6$ | $1.7 \times 10^7$ | 60% |
| 5 | 50 | $1.8 \times 10^7$ | $1.4 \times 10^7$ | $1.9 \times 10^6$ | 10% |
| 7 | 75 | $3.8 \times 10^7$ | $1.7 \times 10^7$ | $1.4 \times 10^7$ | 35% |
| 9 | 50 | $4.9 \times 10^7$ | $1.1 \times 10^6$ | $3.2 \times 10^7$ | 67% |
| 10 | 150 | $5.7 \times 10^7$ | $1.7 \times 10^7$ | $2.4 \times 10^7$ | 41% |

Example 17. Uncultured Amniotic Cell Filtration Method D

Polyester Track Etched (PETE) Membrane (GVS Life Science), a non-woven polyester with a maximum pore size of 10 μm, was used to obtain a population of uncultured cells from batches of pre-filtered amniotic fluid from Donors 4-6, 9, and 10. The same Nalgene™ filtration chamber was assembled. The PETE membrane was cut to fit and placed in the circular membrane support plate (47 mm in diameter). A vacuum line was applied to one of the side ports and the other ports were sealed.

Before each filtration run, a batch of pre-filtered amniotic fluid was removed from refrigeration and brought to room temperature. A small sample was removed to estimate the total number of cells in the batch using a hemocytometer (see Table 4 for results). 20 mL (Donor 4 and 10), 25 mL (Donors 5 and 6), or 30 mL (Donor 9) of pre-filtered amniotic fluid was applied to the upper chamber under vacuum (250 mbar). For Donor 9, the batch of pre-filtered amniotic fluid was partially run through the chamber when it was determined that the membranes had been placed upside-down. The membranes were placed right-side up and the filtrate and remaining pre-filtered sample recombined and filtered as described herein.

After the fluid had been pulled through the chamber, the vacuum was turned off and the device was disassembled. Tweezers were used to remove the membrane. For Donors 4 and 9, the membrane was placed in a dish containing 5 mL of PBS and gently agitated. For Donors 5, 6, and 10, the membrane was placed in a dish containing 5 mL of 0.05% trypsin in PBS for 10 minutes. A cell scraper was used to gently remove the cell layer off of the membrane. The membrane was transferred to an empty dish and the cell scraper was used to gently remove any remaining cells and liquid. The cell suspensions (also called "retentate") were combined into a 50 mL conical tube.

The filtration chamber was reassembled in the same manner as before using the same membrane. The filtration and cell collection steps were repeated until the remainder of the batch of pre-filtered amniotic fluid had been processed. Between each donor fluid processed, the membrane was soaked in warm water with detergent then rinsed and air dried overnight.

A small sample was removed from the combined cell suspension to determine the total number of cells recovered from the membrane using a hemocytometer. The remainder of the retentate was centrifuged at 1200 to 2000 RPM for 20 minutes to pellet the cells. The supernatant was discarded and the cell pellet resuspended in 3 mL (Donors 4, 5, and 9) or 10 mL (Donors 6 and 10) of PBS. The resuspended cells were lyophilized. The filtrate was transferred into 50 mL conical tubes and stored in the freezer. A small sample of the filtrate was removed to determine the total number of cells that were not retained by the sieves. Table 4 summarizes the volume of fluid processed, estimated cell count, and percent cells recovered for filtration of pre-filtered amniotic fluid batches from Donors 4-6, 9, and 10 using the PETE membrane.

TABLE 4

| Donor | Pre-filtered AF batch volume processed (mL) | Estimated Total Cells | | | Percent Cells Recovered |
| --- | --- | --- | --- | --- | --- |
| | | Before filtration | Filtrate | Retentate | |
| 4 | 50 | $3.0 \times 10^7$ | $3.2 \times 10^6$ | $1.7 \times 10^7$ | 58% |
| 5 | 100 | $2.3 \times 10^7$ | $1.6 \times 10^7$ | $1.4 \times 10^6$ | 6% |
| 6 | 150 | $6.1 \times 10^7$ | $2.3 \times 10^7$ | $2.0 \times 10^7$ | 32% |
| 9 | 50 | $4.3 \times 10^7$ | $2.4 \times 10^6$ | $2.5 \times 10^7$ | 58% |
| 10 | 50 | $3.0 \times 10^7$ | $6.0 \times 10^6$ | $8.4 \times 10^6$ | 28% |

Example 18. Uncultured Amniotic Cell Filtration Method E

A set of pluriStrainer® cell strainers (pluriSelect USA, San Diego, Calif.) made of polyethylene terephthalate (PET) and having mesh sizes of 6, 10, 15, 20, and 30 μm were used to obtain a population of uncultured cells from pre-filtered amniotic fluid from Donors 1, 3, 4, and 9. Each cell strainer was inserted into the opening of a 50 mL conical tube held in a stationary rack.

Each batch of pre-filtered amniotic fluid was removed from refrigeration and brought to room temperature prior to filtration. A small sample was removed to estimate the total number of cells in each batch using a hemocytometer. See Table 5. 5 mL of pre-filtered amniotic fluid was added to each strainer and left to pass under gravity through the strainer and into the underlying conical tube, leaving cells trapped behind on the strainer. After the fluid ceased to pass through the strainer, the strainer was flipped over and inserted into a fresh conical tube. The strainers were washed with PBS (volume for volume) to release the cells from the strainer and into the fresh tube.

A small sample of the cell suspension (also called "retentate") was removed and a hemocytometer used to determine the total number of cells recovered from the strainer. A small sample of the filtrate was also removed from the flow-through to determine the total number of cells that were not retained by the strainer. The remainder of the retentate was centrifuged at 1200 to 2000 RPM for 20 minutes to pellet the cells. The supernatant was discarded and the cell pellet resuspended in 3 mL of PBS. The resuspended cells were divided equally into two vials and lyophilized. The filtrate was transferred into 50 mL conical tubes and stored in the freezer. A small sample of the filtrate was removed to determine the total number of cells that were not retained by the sieves. Table 5 summarizes the volume of fluid processed, the size strainer used, estimated cell counts, and percent cells recovered for filtration of pre-filtered amniotic fluid batches from Donors 1, 3, 4, and 9 using the pluriSelect strainers.

TABLE 5

| Donor | Pre-filtered AF batch volume processed (mL) | Strainer size (μm) | Estimated Total Cells Before filtration | Filtrate | Retentate | Percent Cells Recovered* |
|---|---|---|---|---|---|---|
| 1 | 5 | 6 | $3.1 \times 10^6$ | $2.1 \times 10^5$ | $2.5 \times 10^6$ | 79% |
|   | 5 | 10 | $3.1 \times 10^6$ | $2.0 \times 10^5$ | $2.8 \times 10^6$ | 89% |
|   | 5 | 10 | $3.7 \times 10^6$ | $1.9 \times 10^6$ | $5.0 \times 10^5$ | 14% |
| 3 | 3.3 | 6 | $5.8 \times 10^5$ | $3.3 \times 10^4$ | $1.7 \times 10^5$ | 28% |
|   | 3.3 | 10 | $5.8 \times 10^5$ | $5.3 \times 10^4$ | $7.1 \times 10^5$ | 122% |
|   | 4.3 | 15 | $7.6 \times 10^5$ | $2.6 \times 10^4$ | $3.4 \times 10^5$ | 44% |
|   | 1 | 20 | $1.8 \times 10^5$ | $1.2 \times 10^4$ | $1.8 \times 10^4$ | 10% |
|   | 5 | 30 | $8.8 \times 10^5$ | $1.2 \times 10^5$ | $3.7 \times 10^5$ | 42% |
| 4 | 3.2 | 6 | $1.9 \times 10^6$ | $9.6 \times 10^4$ | $7.5 \times 10^5$ | 39% |
|   | 0.6 | 10 | $3.7 \times 10^5$ | $0.4 \times 10^4$ | $6.0 \times 10^5$ | 162% |
|   | 3.5 | 15 | $2.1 \times 10^6$ | $5.6 \times 10^4$ | $9.9 \times 10^5$ | 47% |
|   | 1.7 | 20 | $1.0 \times 10^6$ | $1.7 \times 10^4$ | $6.0 \times 10^5$ | 85% |
|   | 4 | 30 | $2.4 \times 10^6$ | $8.4 \times 10^5$ | $1.1 \times 10^6$ | 73% |
| 9 | 4.5 | 6 | $3.4 \times 10^6$ | $4.4 \times 10^4$ | $2.5 \times 10^6$ | 38% |
|   | 0.8 | 10 | $6.1 \times 10^5$ | $2.0 \times 10^4$ | $6.2 \times 10^5$ | 102% |
|   | 0.8 | 15 | $6.1 \times 10^5$ | $0.4 \times 10^4$ | $1.0 \times 10^6$ | 46% |
|   | 4.9 | 20 | $3.7 \times 10^6$ | $7.0 \times 10^4$ | $3.2 \times 10^6$ | 57% |
|   | 5.3 | 30 | $4.0 \times 10^6$ | $8.6 \times 10^4$ | $3.0 \times 10^6$ | 44% |

*Greater than 100% recovery percentages may be due to cell count variability associated with small processing volumes.

Example 19. Protein Content Following Fractionation

Total protein content was determined for lyophilized cell fractions from Donors 3, 4, and 9 and protein concentration was determined for liquid protein fractions (filtrate) from Donors 1, 3, and 9 following cell fractionation. Total protein was quantified using a Pierce™ BCA Protein Assay Kit (Thermo Scientific™, Product No. 23227), and normalized to dry mass of the lyophilized sample or to the volume of the liquid sample. The lyophilized cell fraction results and liquid protein fraction results are summarized in Tables 6 and 7, respectively.

TABLE 6

| Lyophilized Cell Fraction | | | |
|---|---|---|---|
| Filtration Method | Donor | Total Protein/dry mass (μg/mg) | Mean Total Protein/dry mass (μg/mg) |
| A | 3 | 122 | 100 |
|   | 4 | 78 |   |
| C | 3 | 55 | 40 |
|   | 4 | 115 |   |
|   | 9 | 55 |   |
| D | 3 | 36 | 34 |
|   | 4 | 46 |   |
|   | 9 | 40 |   |

TABLE 6-continued

| Lyophilized Cell Fraction | | | |
|---|---|---|---|
| Filtration Method | Donor | Total Protein/dry mass (μg/mg) | Mean Total Protein/dry mass (μg/mg) |
| E | 3 | 7 | 75 |
|   | 4 | 83 |   |
|   | 9 | 11.6 |   |

TABLE 7

| Liquid Protein Fraction | | | |
|---|---|---|---|
| Donor | Filtration Method | Protein Concentration (μg/mL) | Mean Protein Concentration (μg/mL) |
| 1 | A | 2646 | 2540 |
|   | B | 2435 |   |
| 3 | A | 2194 | 3507 |
|   | C | 4072 |   |
|   | D | 4383 |   |
|   | E | 3378 |   |
| 9 | C | 2116 | 2148 |
|   | D | 2102 |   |
|   | E | 2225 |   |

Example 20. Hemoglobin and Urea Content in Filtered, Lyophilized, Uncultured Amniotic Cells The hemoglobin content of lyophilized cell fractions from Donors 5-8, and 10 and unfiltered amniotic fluid samples from Donors 6 and 8 was measured using a RayBio® Human Hemoglobin ELISA kit (RayBiotech, Product No. ELH-Hgb1). Lyophilized samples were prepared as 35 mg dry mass in 1 mL of 1× lysis buffer (R&D Systems, Product No. 895347) in PBS. Manufacturer's instructions were followed and hemoglobin levels calculated using the standard curve generated. The limit of detection (LOD) for the hemoglobin assay as performed was considered to be 0.043

μg/mg, based on reconstitution of 35 mg of sample in 1 mL of PBS and the lowest detectable hemoglobin concentration for the ELISA kit being 1.5 μg/mL.

The urea content of lyophilized cell fractions from Donors 5-8, and 10 and unfiltered amniotic fluid samples from Donors 6 and 8 was measured using a Human Urea Nitrogen Detection Kit (Innovative Research, Catalog No. IRAAKT2539). Lyophilized samples were prepared as 35 mg dry mass in 1 mL of 1× lysis buffer (R&D Systems, Product No. 895347) in PBS. Samples were loaded according to the manufacturer's instructions. Urea nitrogen levels were calculated using the standard curve generated from the readings. The limit of detection (LOD) for the urea nitrogen assay as performed was considered to be 0.016 μg/mg, based on the lowest detectable urea nitrogen listed for the ELISA kit being 0.065 mg/dL.

The hemoglobin and urea content results are summarized in Table 8.

philized cell fraction samples tested that were processed using Method D (Donor 5), but expression was not detected in any of the 5 lyophilized cell fractions tested that were processed using Method A. Expression of c-kit was detected in 1 out of 2 freshly filtered fluid cell fractions tested that were processed using Method C using pre-filtered amniotic fluid from Donor 3. The minimum detectable range listed by the manufacturer is 0.057-0.339 ng/mL.

The freshly filtered fluid cell fractions were collected off BioDesign filters by soaking each of the filters (5 um & 10 um) in separate dishes that each contained 5 mL of 0.025% trypsin solution in PBS for 5 minutes. The cell solutions from the two dishes were combined for a total volume of 10 mL cell suspension. The cells were spun down at 500×g for 20 minutes and resuspended in 1 mL of 1× cell lysis buffer (R&D Systems, Catalog No. 895347). Samples were vortexed in the lysis buffer at room temperature and the C-kit ELISA run according to the manufacturer's methods. Lyo-

TABLE 8

| Donor | Filtration Method | Hemoglobin | | Urea | | |
|---|---|---|---|---|---|---|
| | | Total μg | Total μg/mg sample | Total μg | Percent Reduction* | Total μg/mg sample |
| 5 | A | ND | | 9 | | 0.1 |
|   | D | ND | | ND | | |
| 6 | Unfiltered AF | 31 | | 185 | | N/A |
|   | A | ND | | 69 | 63% | 0.5 |
|   | D | ND | | 37 | 80% | 0.4 |
| 7 | A | 775 | 4.8 | 50 | | 0.3 |
|   | C | 515 | 3.2 | ND | | |
|   | D | 32 | 0.2 | 39 | | 0.3 |
| 8 | Unfiltered AF | 60 | | 32 | 100% | N/A |
|   | A | 1 | 0.01 | ND | | |
| 10 | C | ND | | 13 | | 0.1 |
|   | D | ND | | 7.5 | | 0.2 |

*Percent seduction in urea was calculated based on the reduction in total urea between the unfiltered amniotic fluid and lyophilized cell fraction of the same donor.
ND = not detected

Example 21. Particle Size of Lyophilized, Filtered, Uncultured Amniotic Cells The size of particles from a sample of lyophilized, filtered, uncultured amniotic cells (Donor 10 using the BioDesign sieves filtration Method C described above) was estimated to range from about 4 to 212 μm, with a mean size of about 26 μm. To estimate particle size, lyophilized particles were scattered onto a microscope slide and a cover slip placed on top. Calibrated images were captured using a Leica LAS EZ program and analyzed using Image J version 1.50i software. Scaled lines were drawn over the largest diameter of each particle having discernable edges to generate size measurements. A total of 110 particles over 6 images were measured to obtain the mean size and size range.

Example 22. c-Kit Expression in Amniotic Cell Fractions

Expression of c-kit was detected in four of fourteen processed samples tested (fluid or lyophilized cell fractions) and in the two samples of unfiltered, unprocessed amniotic fluid tested (Donor 3 and 11) using a Human CD117/c-kit Quantikine ELISA Kit (R&D Systems, Catalog No. DSCR00). Expression of c-kit was detected in 2 out of 4 lyophilized cell fraction samples tested that were processed using Method C (Donors 3 and 10), and 1 out of 3 lyophilized cell samples were prepared as 35 mg dry weight in 1 mL of 1× lysis buffer (R&D Systems, Catalog No. 895347) in PBS. The c-kit ELISA was run according to the manufacturer's methods.

Example 23. Culture of Filtered Amniotic Cells

A sample of uncultured amniotic cells was obtained from Donor 10 using the 10 μm PETE membrane filtration Method D described above. The cells were plated on polystyrene culture dishes and cultured in DMEM with 20% fetal bovine serum and 1% penicillin-streptomycin. Plastic-adherent cells were observed after 8 and 20 days of culture.

Example 24. Amniotic Fluid Protein Filtration Method

The VivaFlow 200 flipflow filtration unit (Satorius, Sigma-Aldrich) was used to obtain amniotic fluid protein fractions from pooled filtrates retained from the cell filtration methods described above. Those pooled filtrates are referred to as Stage 0 Fractions. Filtrates retained from Donor 1 processed using Cell Filtration Methods A and C were pooled, filtrates from Donor 3 processed using Cell Filtration Methods A, C, D, and E were pooled, and filtrates from Donor 9 processed using Cell Filtration Methods C, D, and E were pooled. A small sample from each Stage 0 Fraction was retained as a control.

For Stage 1, the VivaFlow system was assembled according to the manufacturer's instructions with a polyethersulfone (PES) membrane having a 100 kDa molecular weight cutoff (MWCO). The membrane was flushed with 500 mL of deionized water. The system was drained and the filtrate vessel emptied. The feedline was submerged into the reservoir/return vessel containing the Stage 0 Fraction and vacuum pressure applied (about 2 bars). The system was run until most of the sample had entered the filtrate collection vessel and only a small amount of sample remained in the reservoir/return vessel. A sample of the Stage 1 Filtrate was removed for testing and the remainder stored at refrigeration temperature until Stage 2. A small sample from the return fluid remaining in the reservoir/return vessel was taken and stored before the remaining fluid was discarded. The system was cleaned according to the manufacturer's instructions for a PES membrane.

For Stage 2, a 10 kDa MWCO Hydrosart™ membrane was connected to the system according to the manufacturer's instructions and flushed with 500 mL of deionized water. The system was drained and the filtrate vessel emptied. The feedline was submerged into the reservoir/return vessel containing the Stage 1 Filtrate and vacuum pressure applied (about 2 bars). The system was run until about half of the Stage 1 Filtrate was left in the reservoir/return vessel. To recover protein remaining on membrane, the fluid in the system was pumped in reverse into the reservoir/return vessel and the system reverse-flushed with 20 mL of PBS, which was also collected in the reservoir/return vessel. A sample of the Stage 2 Return was removed for testing and the remainder stored at refrigeration temperature until samples were lyophilized at Stage 3. The system was cleaned and stored according to the manufacturer's instructions for a Hydrosart™ membrane before the next batch run.

Example 25. SDS-PAGE of Amniotic Fluid Protein Fractions

Figure 2:
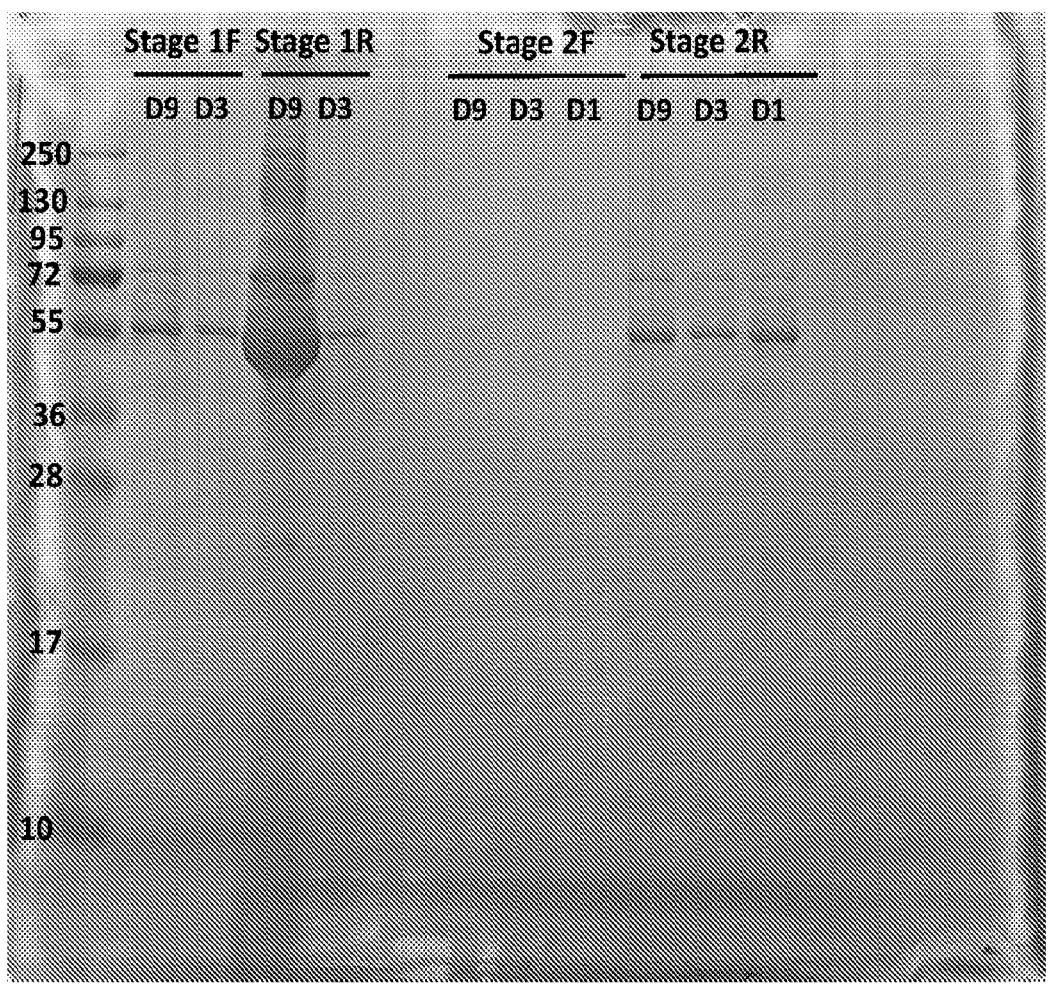
FIG. 2 provides SDS-PAGE analysis of Stage 1 Filtrate, Stage 1 Return, Stage 2 Filtrate, and Stage 2 Return for Donors 1, 3, and 9.

Amniotic fluid protein fractions from Donors 1, 3, and 9 (Stage 0, Stage 1 Filtrate, Stage 1 Return, Stage 2 Filtrate, Stage 2 Return, Stage 3 Lyophilized Product) were characterized by SDS-PAGE. Samples of the liquid fractions were prepared at a 1:1 ratio with SDS sample buffer. Samples of the lyophilized fractions were resuspended in PBS to a concentration of 35 mg/mL and then prepared at a 1:1 ratio with SDS sample buffer. 15-20 μL of each protein sample was loaded into a 10% SDS-PAGE gel alongside 10 μL of a pre-stained protein ladder. The separated proteins were visualized with Coomassie Blue stain and imaged as FIGS. 1 and 2. The protein fractions derived from the Stage 0 Fractions that passed through the 100 kDa filter and were retained by the 10 kDa filter (Stage 2 Return and Stage 3) included visible bands ranging in molecular weight from 10 kDa to 95 kDa (as observed by SDS-PAGE under reducing conditions).

Example 26. Particle Size of Lyophilized Amniotic Fluid Protein Fractions

The size of particles from a sample of lyophilized amniotic fluid protein fraction (Donor 4 Stage 3) was estimated to range from about 5 to 62 μm, with a mean size of about 22 μm. To estimate particle size, lyophilized particles were tapped onto microscope slides to scatter the particles and a cover slip placed over the surface. Calibrated images were captured with Leica LAS EZ program and analyzed using Image J version 1.50i software. Scaled lines were drawn over the largest diameter of each particle having discernable edges to generate size measurements. A total of 86 particles over 6 images were measured to obtain the mean particle size and particle size range.

Example 27. Hemoglobin and Urea Content of Amniotic Fluid Protein Fractions

The hemoglobin (Hgb) content and urea content of Stage 0 fluid protein fractions and Stage 3 lyophilized protein fractions for Donors 1, 3, and 9 were measured using the methods described in Example 20, above, and the results are summarized in Table 9.

TABLE 9

| | | Hemoglobin | | | Urea | | |
|---|---|---|---|---|---|---|---|
| Donor | Sample | Total μg | Percent Reduction* | Total μg/mg sample | Total μg | Percent Reduction* | Total mg/mg sample |
| 1 | Stage 0 | 1882 | 44% | N/A | 38 | 97% | N/A |
|   | Stage 3 | 1054 |     | 53  | 1  |     | 0.07 |
| 3 | Stage 0 | 729  | 48% | N/A | 17 | 94% | N/A |
|   | Stage 3 | 380  |     | 1.3 | 1  |     | 0.02 |
| 9 | Stage 0 | 17764 | 88% | N/A | 66 | 97% | N/A |
|   | Stage 3 | 2095 |     | 3.0 | 2  |     | 0.03 |

*Percent reduction was calculated based on the reduction in total hemoglobin or urea between the Stage 0 fluid and Stage 3 lyophilized fraction of the same donor.

Example 28. Protein Content of Amniotic Fluid Protein Fractions

Protein concentration was determined for amniotic fluid protein fractions from Donors 1, 3, and 9 (Stage 0, Stage 1 Filtrate, Stage 2 Filtrate, Stage 2 Return) and total protein content was determined for the corresponding Stage 3 Lyophilized Product. Total protein was quantified using a Pierce™ BCA Protein Assay Kit (Thermo Scientific™, Product No. 23227), and normalized to volume of the liquid sample or to the dry mass of the lyophilized sample. The results are summarized in Table 10.

TABLE 10

| Sample | Donor | Protein Concentration (μg/mL) | Mean Protein Concentration (μg/mL) |
|---|---|---|---|
| Stage 0* | 1 | 2540 | 2732 |
|          | 3 | 3507 |      |
|          | 9 | 2148 |      |
| Stage 1 Filtrate | 1 | 475   | 3758 |
|                  | 3 | 10092 |      |
|                  | 9 | 708   |      |
| Stage 2 Filtrate | 1 | 254 | 243 |
|                  | 3 | 266 |     |
|                  | 9 | 210 |     |
| Stage 2 Return | 1 | 724 | 460 |
|                | 3 | 322 |     |
|                | 9 | 333 |     |

| Sample | Donor | Total Protein/Dry Mass (μg/mg) | Mean Total Protein/Dry Mass (μg/mg) |
|---|---|---|---|
| Stage 3 | 1 | 71 | 67 |
|         | 3 | 72 |    |
|         | 9 | 60 |    |

*Protein concentrations listed for Stage 0 samples are mean concentrations listed in Table 7 determined prior to pooling of donor filtrates for protein fractionation. The average protein concentration for Stage 0 samples is the average of the Stage 0 concentrations listed in this table.

Example 29. Hyaluronic Acid and Lactoferrin

The amount of hyaluronic acid (HA) and lactoferrin (LF) present in samples of Stage 3 Lyophilized Product was determined using ELISA kits (R&D Systems Hyaluronan Quantikine ELISA, Product No. DHIYAL0; AssayPro Assaymax™ Human Lactoferrin ELISA kit, Catalog No. EL2011-1) according to the manufacturer's instructions. The minimum detectable amount of lactoferrin and hyaluronic acid using these methods is 0.35 ng/mL and 0.068 ng/mL respectively. Total HA and lactoferrin was normalized to the dry mass of the lyophilized sample. The results are summarized in Table 11.

TABLE 11

| Donor | Product mass (mg) | Resuspended volume (mL) | Total HA (ng) | Total HA/ dry mass (ng/mg) | Total LF (ng) | Total LF/ dry mass (ng/mg) |
| --- | --- | --- | --- | --- | --- | --- |
| 1 | 23 | 0.6 | ND | ND | 43 | 1.9 |
| 3 | 41 | 1.1 | 33418 | 815 | 82 | 2.0 |
| 9 | 35 | 1 | 1520 | 44 | 93 | 2.7 |

HA was not detectable in the Stage 3 product from Donor 1, but was detectable in the Stage 2 Return fraction.

What is claimed is:

1. A lyophilized product comprising a population of uncultured amniotic cells obtained from amniotic fluid, wherein the product is substantially free of red blood cells, wherein the product does not contain a cryoprotectant, and wherein the product comprises a protein fraction obtained from an amniotic fluid filtrate.

2. The product of claim 1, wherein the protein fraction comprises proteins having a molecular weight less than about 600 kDa.

3. The product of claim 2, wherein the product is substantially free of urea, as determined by a urea nitrogen assay.

4. The product of claim 2, wherein the product is substantially free of hemoglobin, as determined by an enzyme-linked immunosorbent assay.

5. The product of claim 2, wherein the product has a urea content per dry mass of the product of less than about 100 μg/mg, as determined by a urea nitrogen assay.

6. The product of claim 2, wherein the product comprises hyaluronic acid.

7. The product of claim 2, wherein the product is sterilized.

8. The product of claim 2, wherein the protein fraction further comprises proteins having a molecular weight greater than about 600 kDa.

9. The product of claim 2, wherein the product comprises growth factors, glycoproteins, glycosaminoglycans (GAGs), polycarbohydrates, or cytokines.

10. The product of claim 1, wherein the product is substantially free of one or more of urea, electrolytes, amino acids, or peptides consisting of 2 amino acids.

11. The product of claim 1, wherein the population of uncultured amniotic cells comprises amniotic stem cells.

12. The product of claim 1, wherein the population of uncultured amniotic cells comprises adherent cells.

13. The product of claim 1, wherein the population of uncultured amniotic cells comprises c-kit positive cells.

14. The product of claim 1, wherein hemoglobin is not detectable in the product, as determined by an enzyme-linked immunosorbent assay.

15. The product of claim 1, wherein the product is substantially free of urea, as determined by a urea nitrogen assay.

16. The product of claim 1, wherein the product has a urea content per dry mass of the product of less than about 100 μg/mg, as determined by a urea nitrogen assay.

17. The product of claim 1, wherein the amniotic fluid is from a human donor.

18. The product of claim 1, wherein the product comprises hyaluronic acid.

19. The product of claim 1, wherein the product is sterilized.

20. A lyophilized product comprising a population of uncultured amniotic cells obtained from amniotic fluid, wherein the product is substantially free of red blood cells, wherein the product does not contain a cryoprotectant, wherein the product comprises a protein fraction obtained from an amniotic fluid filtrate, wherein the protein fraction comprises proteins having a molecular weight of less than about 600 kDa, and wherein the product is substantially free of one or more of white blood cells, urea, electrolytes, amino acids, or peptides consisting of 2 amino acids.

21. The product of claim 20, wherein the protein fraction further comprises proteins having a molecular weight greater than about 600 kDa.

22. The product of claim 20, wherein the product comprises growth factors, glycoproteins, glycosaminoglycans (GAGs), polycarbohydrates, or cytokines.

23. A pharmaceutical composition comprising the product of claim 1, and a pharmaceutically acceptable carrier.

24. A kit comprising the product of claim 1, and a pharmaceutically acceptable carrier.

25. A method of treating a wound of a subject comprising applying the composition of claim 1 to the wound.

26. A method of treating a wound of a subject comprising applying the composition of claim 2 to the wound.

27. A method of delivering the pharmaceutical composition of claim 23 to skin of a subject comprising topically applying the product or injecting the product into a dermal layer of the skin.

28. A method of treating a wound of a subject comprising applying the pharmaceutical composition of claim 23 to the wound or injecting the product into the wound.

29. A method of delivering the pharmaceutical composition of claim 23 to an eye of a subject comprising topically applying the product to the eye.

30. A method of delivering the pharmaceutical composition of claim 23 to a joint of a subject comprising injecting the product into the joint or applying the product to the joint.

31. A method of delivering the pharmaceutical composition of claim 23 to the spine of a subject comprising injecting the product into the spine or applying the product to the spine.

32. A method of lubricating or cushioning a joint or spine of a subject comprising applying the pharmaceutical composition of claim 23 to the joint or spine, or injecting the product into the joint or spine.

33. A method of reducing inflammation of a joint or spine of a subject comprising applying the pharmaceutical composition of claim 23 to the joint or spine, or injecting the product into the joint or spine.

* * * * *